US009821093B2

(12) United States Patent
Cottone, Jr. et al.

(10) Patent No.: US 9,821,093 B2
(45) Date of Patent: *Nov. 21, 2017

(54) PROGENITOR ENDOTHELIAL CELL CAPTURING WITH A DRUG ELUTING IMPLANTABLE MEDICAL DEVICE

(71) Applicant: OrbusNeich Medical, Inc., Fort Lauderdale, FL (US)

(72) Inventors: Robert John Cottone, Jr., Davie, FL (US); Stephen M. Rowland, Miami, FL (US); Sherry Parker, Sunrise, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,938

(22) Filed: Apr. 23, 2013

(65) Prior Publication Data

US 2013/0295156 A1   Nov. 7, 2013

Related U.S. Application Data

(63) Continuation of application No. 11/560,352, filed on Nov. 15, 2006, now Pat. No. 8,460,367, and a
(Continued)

(51) Int. Cl.
*A61F 2/06* (2013.01)
*A61L 31/10* (2006.01)
(Continued)

(52) U.S. Cl.
CPC .............. *A61L 31/16* (2013.01); *A61L 27/30* (2013.01); *A61L 27/54* (2013.01); *A61L 29/10* (2013.01);
(Continued)

(58) Field of Classification Search
CPC ........................................................ A61F 2/06
(Continued)

(56) References Cited

U.S. PATENT DOCUMENTS 4,355,426 A * 10/1982 MacGregor .................. 623/1.4
5,492,890 A *  2/1996 Ginsberg et al. ............. 514/12
(Continued)

FOREIGN PATENT DOCUMENTS

EP       1355588      10/2003
WO    03/099169      12/2003

OTHER PUBLICATIONS

First Examination Report Issued by Government of India Patent Office on Jun. 21, 2013 in corresponding Indian Application No. 4154/DELNP/2006.
(Continued)

*Primary Examiner* — Yashita Sharma
(74) *Attorney, Agent, or Firm* — Leason Ellis LLP

(57) ABSTRACT

A medical device for implantation into vessels or luminal structures within the body is provided, which stimulates positive blood vessel remodeling. The medical device, such as a stent and a synthetic graft, is coated with a pharmaceutical composition consisting of a controlled-release matrix and one or more pharmaceutical substances for direct delivery of drugs to surrounding tissues. The coating on the medical device further comprises a ligand such as a peptide, an antibody or a small molecule for capturing progenitor endothelial cells in the blood contacting surface of the device for restoring an endothelium at the site of injury. In particular, the drug-coated stents are for use, for example, in balloon angioplasty procedures for preventing or inhibiting restenosis.

15 Claims, 22 Drawing Sheets

Related U.S. Application Data continuation-in-part of application No. 11/076,731, filed on Mar. 10, 2005, which is a continuation-in-part of application No. 10/442,669, filed on May 20, 2003, now abandoned, and a continuation-in-part of application No. 10/360,567, filed on Feb. 6, 2003, now abandoned, which is a continuation-in-part of application No. 09/808,867, filed on Mar. 15, 2001, now Pat. No. 7,037,332.

(60) Provisional application No. 60/822,451, filed on Aug. 15, 2006, provisional application No. 60/736,920, filed on Nov. 15, 2005, provisional application No. 60/382,095, filed on May 20, 2002, provisional application No. 60/354,680, filed on Feb. 6, 2002, provisional application No. 60/201,789, filed on May 4, 2000, provisional application No. 60/189,674, filed on Mar. 15, 2000, provisional application No. 60/551,978, filed on Mar. 10, 2004.

(51) Int. Cl.

| | |
|---|---|
| *A61L 31/16* | (2006.01) |
| *A61L 27/30* | (2006.01) |
| *A61L 27/54* | (2006.01) |
| *A61L 29/10* | (2006.01) |
| *A61L 29/16* | (2006.01) |
| *A61L 31/08* | (2006.01) |
| *C12N 5/071* | (2010.01) |
| *A61L 31/12* | (2006.01) |
| *A61F 2/91* | (2013.01) |

(52) U.S. Cl.
CPC ............... *A61L 29/16* (2013.01); *A61L 31/08* (2013.01); *A61L 31/082* (2013.01); *A61L 31/10* (2013.01); *A61L 31/12* (2013.01); *A61L 31/121* (2013.01); *C12N 5/0692* (2013.01); *A61F 2/91* (2013.01); *A61L 2300/256* (2013.01); *C12N 2510/00* (2013.01)

(58) Field of Classification Search
USPC .......... 623/1.15, 1.34, 1.39, 1.4, 1.42, 1.46, 623/1.48, 23.76
See application file for complete search history.

(56) References Cited

U.S. PATENT DOCUMENTS 5,824,048 A * 10/1998 Tuch .............................. 128/898
5,880,090 A *  3/1999 Hammond et al. ............... 514/2

OTHER PUBLICATIONS

Flugelman, et al. Genetically Engineered Endothelial Cells Remain Adherent and Viable After Stent Deployment and Exposure to Flow In Vitro; Circulation Research vol. 70, No. 2 Feb. 1992 pp. 348-354.

* cited by examiner

FIG. 4A
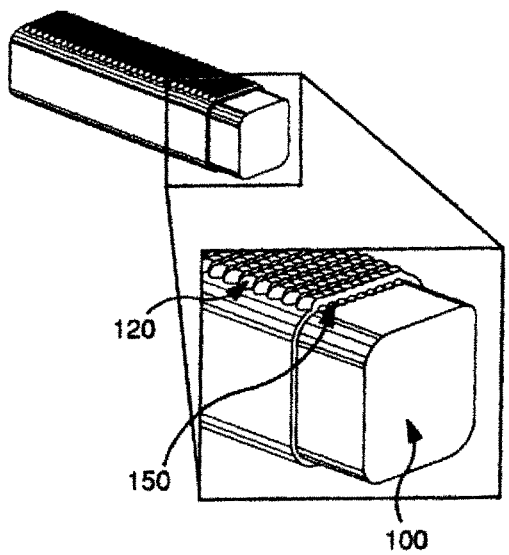
FIG. 4B
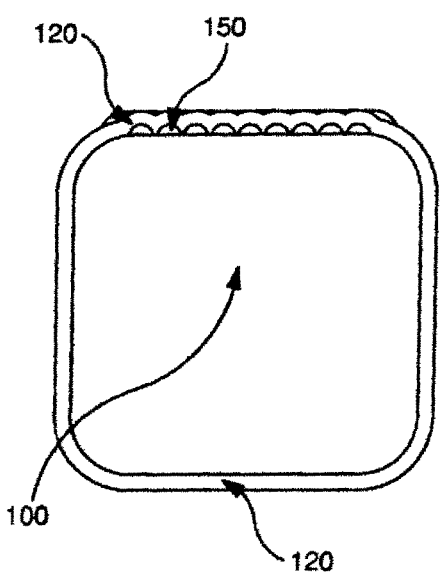
FIG. 4C

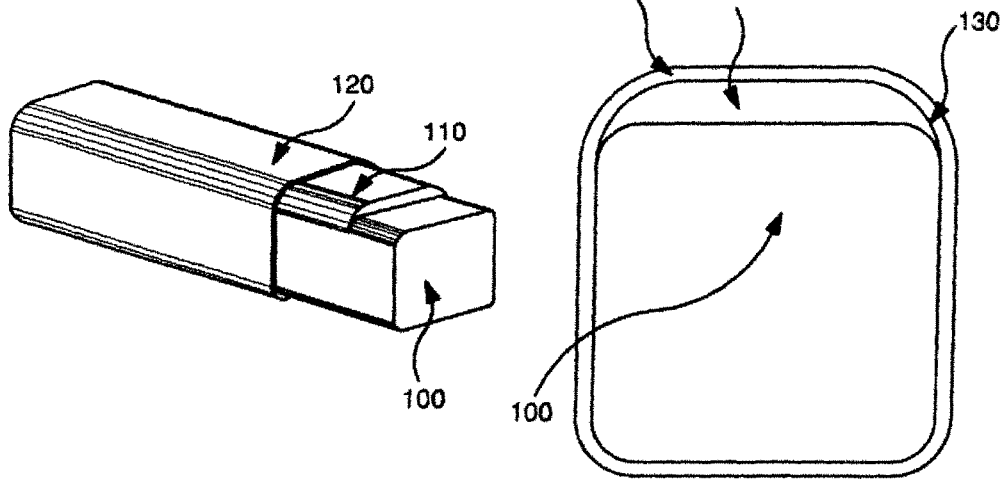
FIG. 5A    FIG. 5B

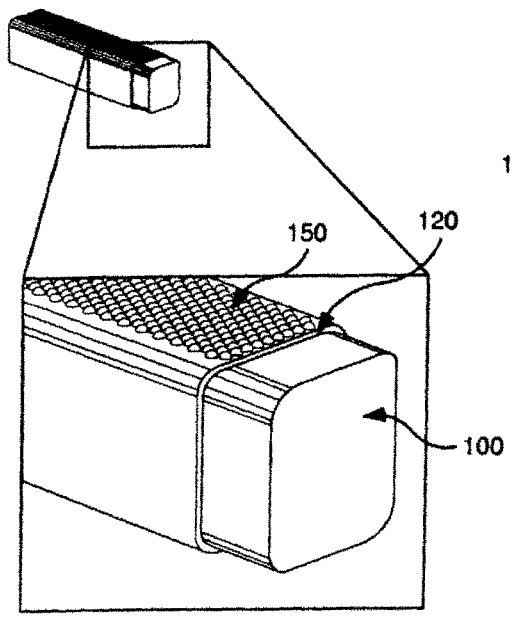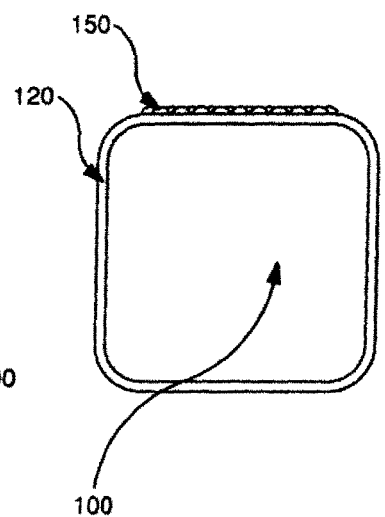
FIG. 6A
FIG. 6B
FIG. 6C

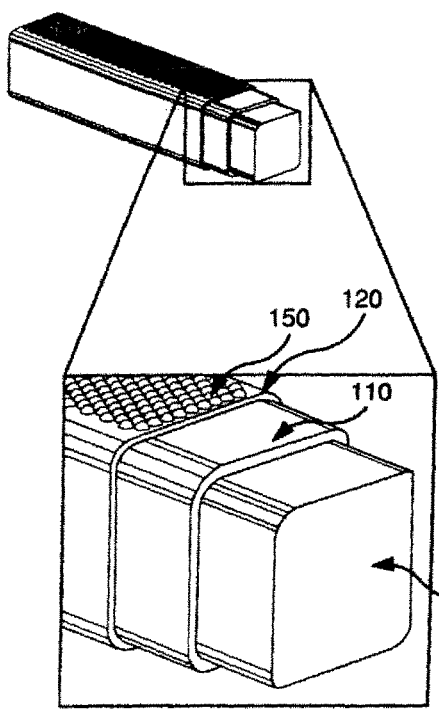
FIG. 7A
FIG. 7B
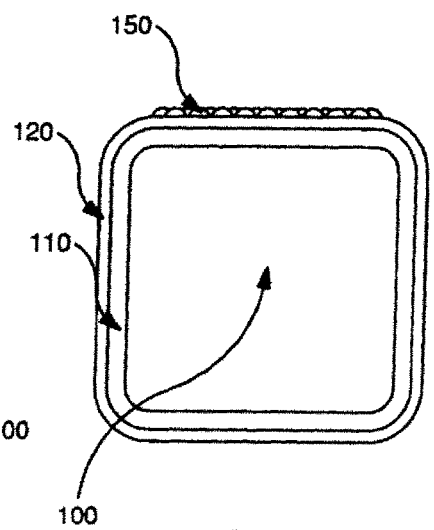
FIG. 7C

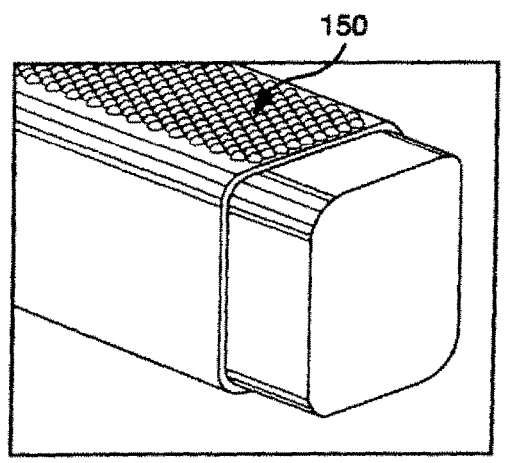 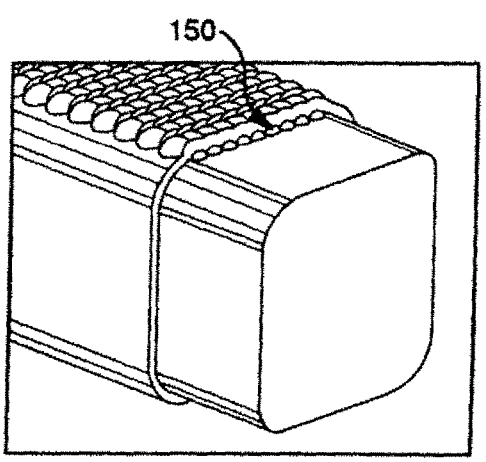
FIG. 8A  FIG. 8B

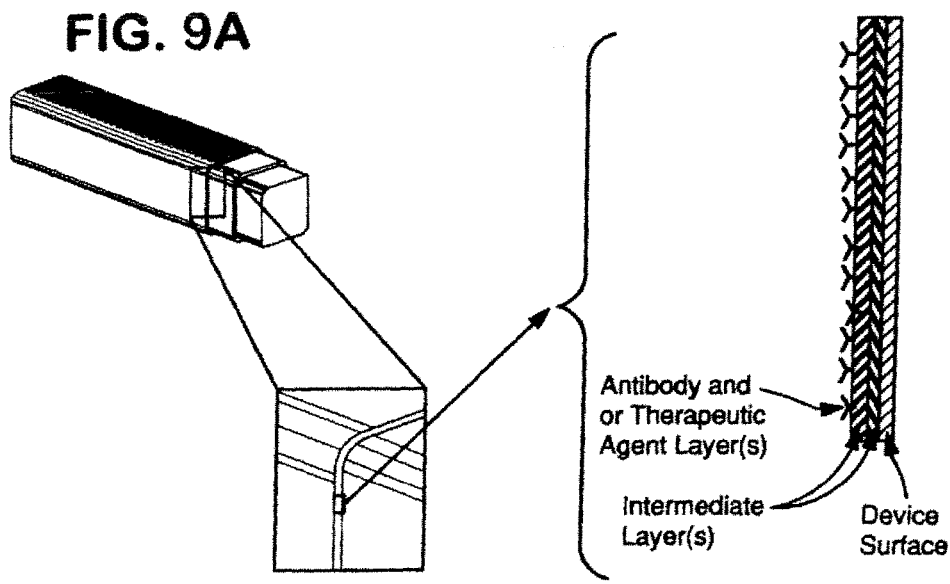

FIG. 10A-1
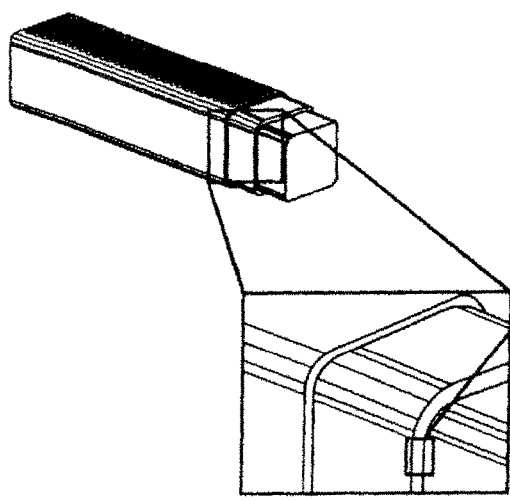
FIG. 10A-2
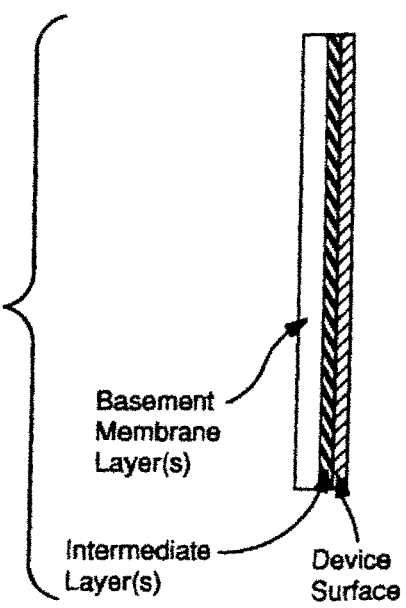
Basement Membrane Layer(s)
Intermediate Layer(s)
Device Surface
FIG. 10A-3

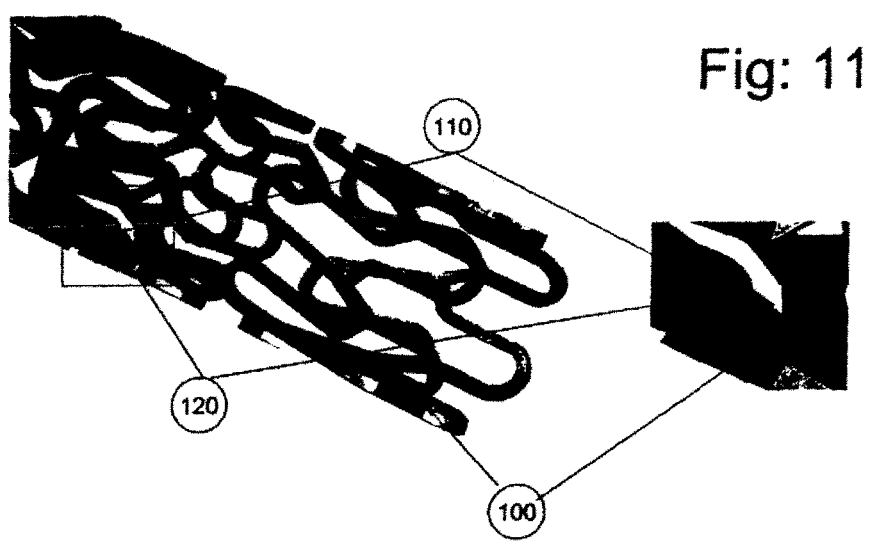
Fig: 11

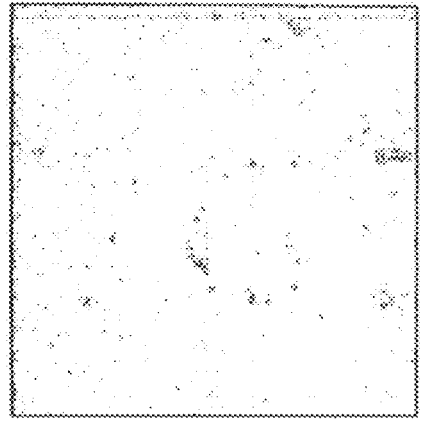 FIG. 20C Bare SST
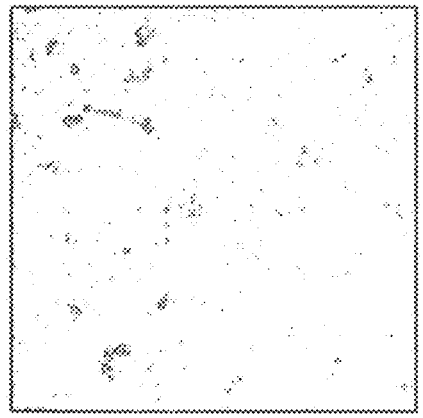 FIG. 20B Gelatin + Ab
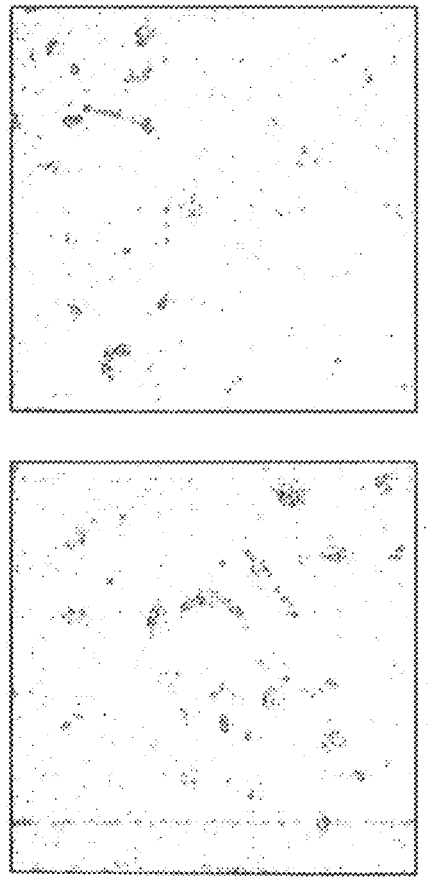 FIG. 20A CMDx + Ab
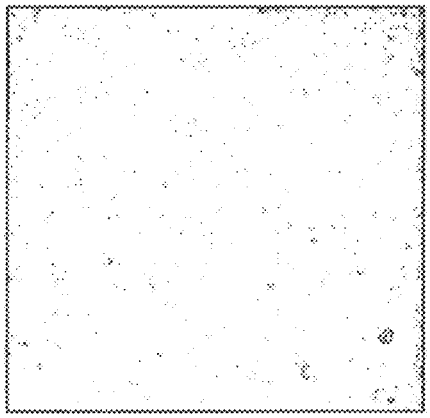 FIG. 20E Gelatin
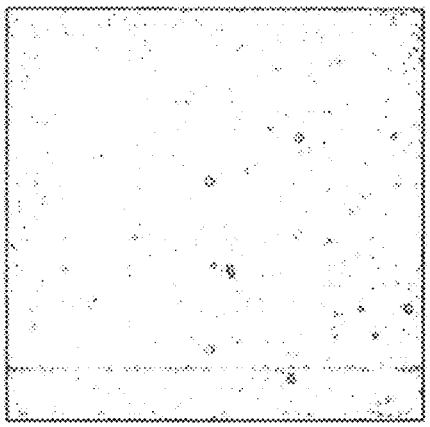 FIG. 20D CMDx
All images at 20X

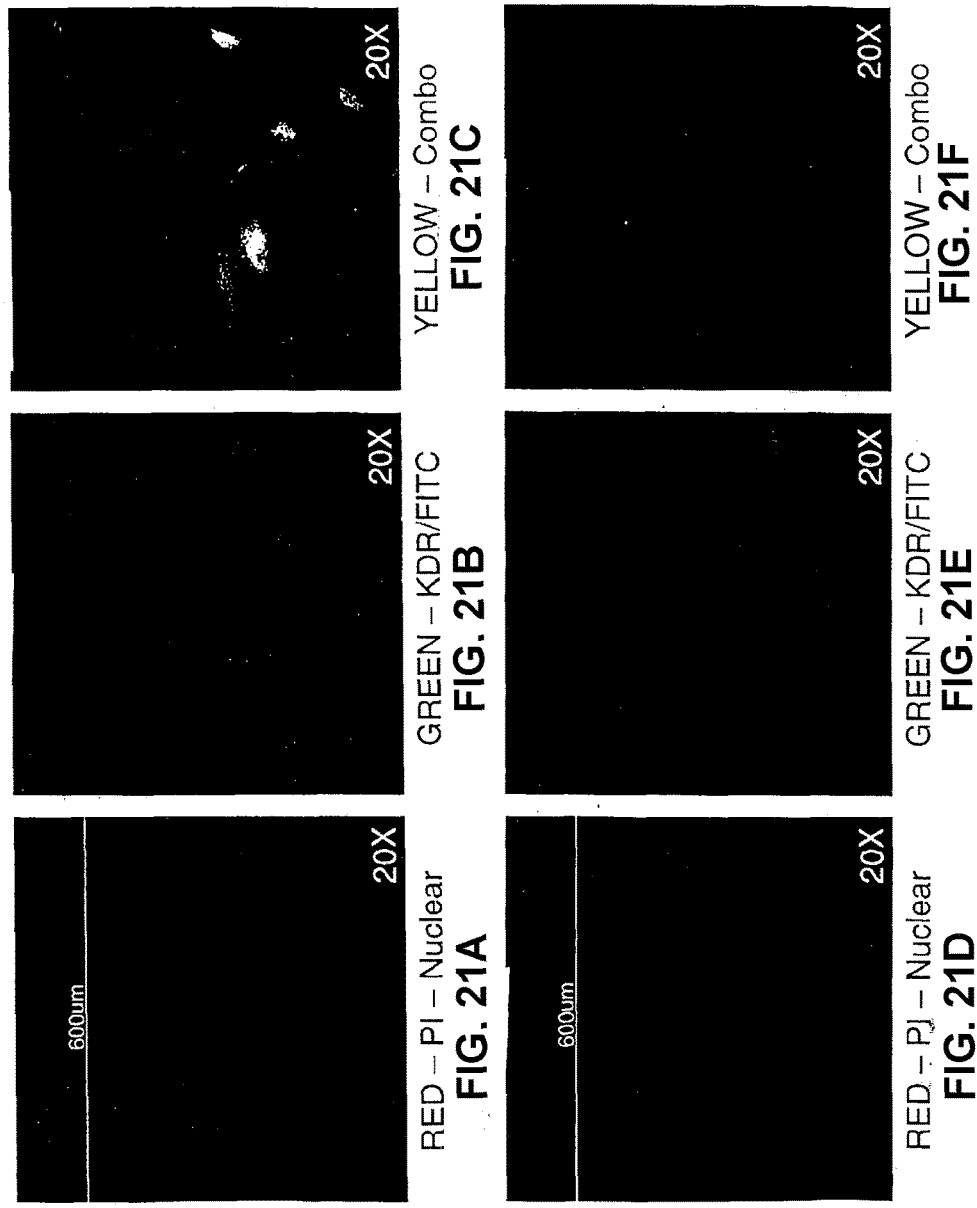
FIG. 21A RED – PI – Nuclear
FIG. 21B GREEN – KDR/FITC
FIG. 21C YELLOW – Combo
FIG. 21D RED – PI – Nuclear
FIG. 21E GREEN – KDR/FITC
FIG. 21F YELLOW – Combo

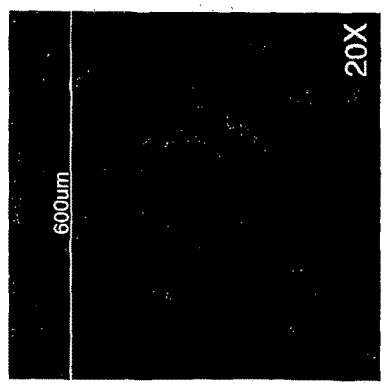
FIG. 22A RED – PI – Nuclear
FIG. 22B GREEN – KDR/FITC
FIG. 22C YELLOW – Combo
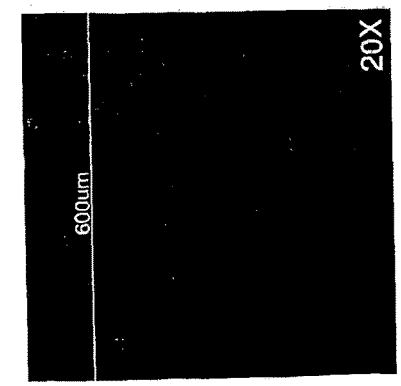
FIG. 22D RED – PI – Nuclear
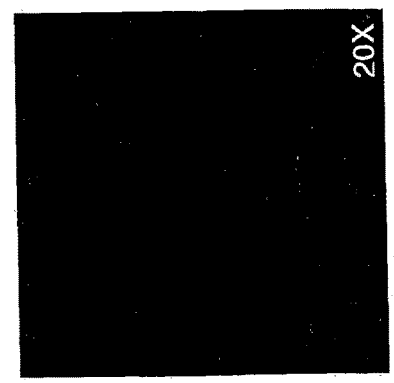
FIG. 22E GREEN – KDR/FITC
FIG. 22F YELLOW – Combo

PROGENITOR ENDOTHELIAL CELL CAPTURING WITH A DRUG ELUTING IMPLANTABLE MEDICAL DEVICE

CROSS REFERENCE TO RELATED APPLICATION

This application is a continuation of U.S. application Ser. No. 11/560,352, filed on Nov. 15, 2006, which is a continuation-in-part of application Ser. No. 11/076,731, filed on Mar. 10, 2005, which is a continuation-in-part application of U.S. application Ser. No. 10/442,669, filed on May 20, 2003 which claims benefit from U.S. Provisional Application Ser. No. 60/382,095, filed on May 20, 2002, and is a continuation-in-part of U.S. application Ser. No. 10/360,567 filed on Feb. 6, 2003, which claims benefit of U.S. Provisional Application No. 60/354,680, filed on Feb. 6, 2002 and is a continuation-in-part of U.S. application Ser. No. 09/808,867, filed on Mar. 15, 2001, which claims benefit of U.S. Provisional Application Ser. No. 60/189,674, filed on Mar. 15, 2000 and U.S. Provisional Application 60/201,789, filed on May 4, 2000. This application also claims benefit of U.S. Provisional Ser. No. 60/736,920, filed Nov. 15, 2005 and U.S. Provisional Ser. No. 60/822,451, filed Aug. 15, 2006. The disclosures of all of these applications are herein incorporated by reference in their entirety.

BACKGROUND OF INVENTION

The invention relates to a medical device for implantation into vessels or luminal structures within the body. More particularly, the present invention relates to stents and synthetic grafts with a coating comprising a controlled-release matrix comprising a pharmaceutical composition with a medicinal substance or drug for direct delivery to the surrounding tissues, and a ligand for capturing target cells in vivo. The pharmaceutical composition in the coating can comprise one or more drugs with similar or different effects on particular cells or tissues, for example, to inhibit smooth muscle cell migration and proliferation; and/or stimulate and maintain positive blood vessel remodeling in the treatment of diseases such as restenosis, artherosclerosis, and endoluminal reconstructive therapies.

Atherosclerosis is one of the leading causes of death and disability in the world. Atherosclerosis involves the deposition of fatty plaques on the luminal surface of arteries. The deposition of fatty plaques on the luminal surface of the artery causes narrowing of the cross-sectional area of the artery. Ultimately, this deposition blocks blood flow distal to the lesion causing ischemic damage to the tissues supplied by the artery.

Coronary arteries supply the heart with blood. Coronary artery atherosclerosis disease (CAD) is the most common, serious, chronic, life-threatening illness in the United States, affecting more than 11 million persons. The social and economic costs of coronary atherosclerosis vastly exceed that of most other diseases. Narrowing of the coronary artery lumen causes destruction of heart muscle resulting first in angina, followed by myocardial infarction and finally death. There are over 1.5 million myocardial infarctions in the United States each year. Six hundred thousand (or 40%) of those patients suffer an acute myocardial infarction and more than three hundred thousand of those patients die before reaching the hospital. (*Harrison's Principles of Internal Medicine*, 14$^{th}$ Edition, 1998).

CAD can be treated using percutaneous transluminal coronary balloon angioplasty (PTCA). More than 400,000 PTCA procedures are performed each year in the United States. In PTCA, a balloon catheter is inserted into a peripheral artery and threaded through the arterial system into the blocked coronary artery. The balloon is then inflated, the artery stretched, and the obstructing fatty plaque flattened, thereby increasing the cross-sectional flow of blood through the affected artery. The therapy, however, does not usually result in a permanent opening of the affected coronary artery. As many as 50% of the patients who are treated by PTCA require a repeat procedure within six months to correct a re-narrowing of the coronary artery. Medically, this re-narrowing of the artery after treatment by PTCA is called restenosis.

Restenosis can involve recoil and shrinkage of the vessel. Subsequently, recoil and shrinkage of the vessel are followed by proliferation of medial smooth muscle cells in response to injury of the artery from PICA, which causes a narrowing of the inner lumen diameter of the blood vessel and thereby causing a decrease in blood flow distal to the injury. In response to blood vessel injury, smooth muscle cells in the tunica media and fibroblasts of the adventitial layer undergo phenotypic change which results in the secretion of metalloproteases into the surrounding matrix, luminal migration, proliferation and protein secretion. Various other inflammatory factors are also released into the injured area including thromboxane $A_2$, platelet derived growth factor (PDGF) and fibroblast growth factor (FGF) (Francki et al. *Am. J. Pathol.* 1995 November; 147(5): 1372-82; Raines E. W. *Cytokine Growth Factor Rev.* 2004 August; 15(4): 237-254). A number of different techniques have been used to overcome the problem of restenosis, including treatment of patients with various pharmacological agents or mechanically holding the artery open with a stent. (*Harrison's Principles of Internal Medicine*, 14$^{th}$ Edition, 1998). Initial attempts at preventive therapy that targeted smooth muscle cell proliferation proved ineffective. It has become apparent that to be effective earlier events in the restenotic process must be targeted and subsequent approaches focused on the inhibition of cell regulatory pathways using genetic therapies. Unfortunately, none of these therapies have shown promise for the prevention of restenosis. This lack of success of molecular techniques has led to a revival in the interest of conventional pharmacotherapeutic approaches.

Of the various procedures used to overcome negative remodeling of the blood vessels such as restenosis, stents have proven to be the most effective. Stents are tubular scaffolds typically made of metal or polymers which are positioned in the diseased vessel segment to re-establish a normal vessel inner lumen. Placement of the stent in the affected arterial segment prevents recoil and subsequent reduction of blood flow through the artery. Stents can also prevent local dissection of the artery along the medial layer of the artery. By maintaining a larger lumen than that created using PTCA alone, stents reduce restenosis by as much as 30%. Despite their success, stents have not eliminated restenosis entirely. (Suryapranata et al. 1998. Randomized comparison of coronary stenting with balloon angioplasty in selected patients with acute myocardial infarction. *Circulation* 97:2502-2502).

Narrowing of the arteries can occur in vessels other than the coronary arteries, including carotid, aortoiliac, infrainguinal, distal profunda femoris, distal popliteal, tibial, subclavian and mesenteric arteries. The prevalence of peripheral artery atherosclerosis disease (PAD) depends on the particular anatomic site affected as well as the criteria used for diagnosis of the occlusion. Traditionally, physicians have used the test of intermittent claudication to determine whether PAD is present. However, this measure may vastly underestimate the actual incidence of the disease in the population. Rates of PAD appear to vary with age, with an increasing incidence of PAD in older individuals. In addition, there is an increased prevalence of cerebrovascular disease among patients with PAD.

PAD can be treated using percutaneous translumenal balloon angioplasty (PTA). The use of stents in conjunction with PTA decreases the incidence of restenosis. However, the post-operative results obtained with medical devices such as stents do not match the results obtained using standard operative revascularization procedures, i.e., those using a venous or prosthetic bypass material. (*Principles of Surgery*, Schwartz et al. eds., Chapter 20, *Arterial Disease*, 7th Edition, McGraw-Hill Health Professions Division, New York 1999).

Preferably, PAD is treated using bypass procedures where the blocked section of the artery is bypassed using a graft. (*Principles of Surgery*, Schwartz et al. eds., Chapter 20, *Arterial Disease*, 7th Edition, McGraw-Hill Health Professions Division, New York 1999). The graft can consist of an autologous venous segment such as the saphenous vein or a synthetic graft such as one made of polyester, polytetrafluoroethylene (PTFE), or expanded polytetrafluoroethylene (ePTFE). The post-operative patency rates depend on a number of different factors, including the luminal dimensions of the bypass graft, the type of synthetic material used for the graft and the site of outflow. Restenosis and thrombosis, however, remain significant problems even with the use of bypass grafts. For example, the patency of infrainguinal bypass procedures at 3 years using an ePTFE bypass graft is 54% for a femoral-popliteal bypass and only 12% for a femoral-tibial bypass. Consequently, there is a significant need to improve the performance of both stents and synthetic bypass grafts in order to further reduce the morbidity and mortality of CAD and PAD.

With stents, the approach has been to coat the stents with various antithrombotic or anti-restenotic agents in order to reduce thrombosis and restenosis. For example, impregnating stents with radioactive material appears to inhibit restenosis by inhibiting migration and proliferation of myofibroblasts. (U.S. Pat. Nos. 5,059,166, 5,199,939 and 5,302,168). Irradiation of the treated vessel can pose safety problems for the physician and the patient. In addition, irradiation does not permit uniform treatment of the affected vessel.

Alternatively, stents have also been coated with chemical agents such as heparin or phosphorylcholine, both of which appear to decrease thrombosis and restenosis. Although heparin and phosphorylcholine appear to markedly reduce restenosis in animal models in the short term, treatment with these agents appears to have no long-term effect on preventing restenosis. Additionally, heparin can induce thrombocytopenia, leading to severe thromboembolic complications such as stroke. Therefore, it is not feasible to load stents with sufficient therapeutically effective quantities of either heparin or phosphorylcholine to make treatment of restenosis in this manner practical.

Synthetic grafts have been treated in a variety of ways to reduce postoperative restenosis and thrombosis. (Bos et al. 1998. Small-Diameter Vascular Graft Prostheses: Current Status *Archives Physio. Biochem.* 106:100-115). For example, composites of polyurethane such as meshed polycarbonate urethane have been reported to reduce restenosis as compared with ePTFE grafts. The surface of the graft has also been modified using radiofrequency glow discharge to add polyterephalate to the ePTFE graft. Synthetic grafts have also been impregnated with biomolecules such as collagen.

The arterial wall is not a rigid tube, but rather an organ capable of reshaping in response to hemodynamic, mechanical, and biochemical stimuli. It is known that blood vessels enlarge to accommodate increasing flow to the organ they supply downstream. An example of this process is the enlargement of coronary vessels during natural growth or in left ventricular hypertrophy of the heart. Interest in this phenomenon was stimulated by histological observations that radial enlargement of vessels (outward or positive remodeling) can compensate for progressive growth of atherosclerotic plaques, thus postponing the development of flow-limiting stenosis (Armstrong et al. *Arteriosclerosis* 5:336-346, 1985 and Glagov et al. *N. Eng. J. Med.* 316: 1371-75, 1987). These pathological findings were subsequently supported by in vivo intravascular ultrasound (IVUS) studies that revealed the ubiquitous occurrence of outward remodeling in the presence of atheroma and how such outward remodeling could hide sizable plaques from angiographic detection (Hermiller et al. *Am. J. Cardiol.* 71: 665-668, 1993 and Alfonso et al. *Am. Heart J.* 127: 536-544, 1994).

Although most atherosclerotic segments exhibit some compensatory enlargement, it is often inadequate to completely preserve lumen size, and some vessels may paradoxically shrink at the lesion site (inward or negative remodeling), exacerbating rather than compensating for lumen loss (Nishioka et al. *J. Am. Coll. Cardiol.* 27:1571-1576, 1996 and Pasterkamp et al. *Circulation* 91:1444-1449). This type of constrictive remodeling is reported to occur in 24% to 42% of culprit lesions in coronary arteries (Smits et al. Heart 82: 461-464, 1999 and von Birgelen et al. *J. Am. Coll. Cardiol.* 37: 1864-1870, 2001). The clinical importance of negative remodeling is highlighted by the observation that luminal stenosis correlates more closely with the direction and magnitude of remodeling than with plaque size (Pasterkamp et al. *Circulation* 91:1444-1449, 1995 and Pasterkamp et al. *Arteribscl. Thromb. Vasc. Biol.* 17: 3057-3063, 1997).

In normal arteries, remodeling is a homeostatic response to changes in the flow and circumferential stretch to restore normal shear stress and wall tension, respectively (Langille *Can. J. Physiol. Pharmacol.* 74: 834-841, 1996). High flow demand through conduit arteries induces outward remodeling. This is illustrated in the work of Tronc et al. (*Arterioscler. Thromb. Vast. Biol.* 16: 1256-1262, 1996) where blood flow through the common carotid was elevated surgically using an arterio-venous (a-v) shunt. It has also been shown that outward remodeling occurs in response to increased flow in coronary arteries from atherosclerotic monkeys (Kramsch et al. *N. Engl. J. Med.* 305: 1483-1489, 1981).

Outward remodeling in response to increased flow appears to be largely dependent on shear-responsive endothelial production of nitric oxide and the matrix metalloproteinases (MMPs; Tronc. et al. ibid and Abbruzzese et al. *Surgery* 124: 328-334, 1998). The effect of stretch on remodeling is less clear. Most of the mediators of shear-sensitive remodeling are also stretch responsive, and significant interaction between stretch and shear signals appears to exist (Lehoux et al. *Hypertension* 32:338-345, 1998). Vessel elasticity appears to be the chief determinant of resting vessel size, and recent data suggest that altered production of elastin by cells at the diseased arterial segment may also be involved in remodeling (Di Stefano et al. *J. Vasc. Res.* 35: 1-7, 1998).

Data from animal and human studies indicate that negative remodeling and restenosis may be accentuated by low flow (Krams et al. *Semin. Intervent. Cardiol.* 3: 39-44, 1998 and Serruys et al. *Circulation* 96: 3369-3377, 1997). In low flow states, accentuated production of mitogenic and fibrogenic growth factors such as platelet derived growth factor and transforming growth factor-β, appears to mediate inward (negative) remodeling by increasing smooth muscle cell proliferation and collagen deposition and cross-linking, whereas metalloproteinase induction helps to reorganize vessel structure (Mandy et al. *Cir. Res.* 81: 320-327, 1997 and Bassiouny et al. *Circulation* 98: 157-163, 1998).

The presence of cardiac risk factors affects the remodeling process. For instance, inadequate positive remodeling and negative remodeling are more common in insulin-using than non-insulin-using diabetics and in smokers compared with non-smokers (Komowski et al. *Am. J. Cardiol.* 81: 1298-1304, 1998 and Tauht et al. *Am. J. Cardiol.* 80: 1352-1355, 1997). Paradoxically, negative remodeling is less frequent in those with hypercholesterolemia (Tauth et al. ibid).

Transplant vasculopathy, the most common cause of graft failure and death after heart transplantation, is characterized by diffuse angiographic narrowing which is frequently not amenable to revascularization. Recently, it has become apparent that in addition to progressive intimal thickening, negative or inadequate positive remodeling is common in transplanted hearts, and the importance of its contribution to lumen loss increases with time from transplantation (Lim et al. *Circulation* 95: 885-859, 1997) Despite diffuse endothelialopathy, some remodeling in response to hemodynamic stimuli appears to persist (Allen-Auerbach et al. *J. Heart Lung Transplant* 18: 211-219, 1999). Positive remodeling is also critical for arteriogenesis in the adult. Arteriogenesis refers to the formation of mature arterioles or arteries, lined by smooth muscle cells. The formation or recruitment of collateral vessels is an example of arteriogenesis. While angiogenesis (the sprouting of conduits from existing vessels) is highly stimulated by oxygen deprivation or hypoxia, there is mounting evidence that increased blood flow through the feeder vessel is the important hemodynamic stimulus initiating arteriogenesis. Various experimental studies have hypothesized that an increase in shear rate by local infusion of certain cytokines, or by arterial ligation, as a stimulus for arteriogenesis (Arras et al. *J. Clin. Investi.* 101:40-50, 1998; Egginton et al. *Cardiovasc. Res.* 49: 634-646, 2001; Scholz et al *Virchows Arch.* 436: 257-270, 2000 and Van Royen et al. *J. Nucl. Cardiol.* 8: 687-693, 2001).

The endothelial cell (EC) layer lining blood vessels is a crucial component of the normal vascular wall and provides an interface between the bloodstream and the surrounding tissue of the blood vessel wall. Endothelial cells are also involved in physiological events including angiogenesis, inflammation and the prevention of thrombosis (Rodgers G M. *FASEB J* 1988; 2:116-123.). In addition to the endothelial cells that compose the vasculature, recent studies have revealed that ECs and progenitor endothelial cells circulate postnatally in the peripheral blood (Asahara T, et al., *Science* 1997; 275:964-7; Yin A H, et al. *Blood* 1997; 90:5002-5012; Shi Q, et al. *Blood* 1998; 92:362-367; Gehling U M, et al. *Blood* 2000; 95:3106-3112; Lin Y, et al. *J Clin Invest* 2000; 105:71-77). Progenitor endothelial cells are believed to migrate to regions of the circulatory system with an injured endothelial lining, including sites of traumatic and ischemic injury (Takahashi T, et al. *Nat Med* 1999; 5:434-438). In normal adults, the concentration of progenitor endothelial cells in peripheral blood is 3-10 cells/mm$^3$ (Takahashi T. et al. *Nat Med* 1999; 5:434-438; Kalka C, et al. *Ann Thorac Surg.* 2000; 70:829-834). It is now evident that each phase of the vascular response to injury is influenced (if not controlled) by the endothelium. It is believed that the rapid re-establishment of a functional endothelial layer on damaged stented vascular segments may help to prevent these potentially serious complications by providing a barrier to circulating cytokines, preventing adverse effects of a thrombus, and by the ability of endothelial cells to produce substances that passivate the underlying smooth muscle cell layer. (Van Belle et al. 1997. Stent Endothelialization, *Circulation* 95:438-448; Bos et al. 1998. Small-Diameter Vascular Graft Prostheses: Current Status, *Archives Physio. Biochem.* 106:100-115).

Endothelial cells have been encouraged to grow on the surface of stents by local delivery of vascular endothelial growth factor (VEGF), an endothelial cell mitogen, after implantation of the stent (Van Belle et al. 1997. Stent Endothelialization. *Circulation* 95:438-448.). While the application of a recombinant protein growth factor, VEGF in saline solution at the site of injury induces desirable effects, the VEGF is delivered to the site of injury after stent implantation using a channel balloon catheter. This technique is not desirable since it has demonstrated that the efficiency of a single dose delivery is low and produces inconsistent results. Therefore, this procedure cannot be reproduced accurately every time.

Synthetic grafts have also been seeded with endothelial cells, but the clinical results with endothelial seeding have been generally poor, i.e., low post-operative patency rates (Lio et al. 1998. New concepts and Materials in Microvascular Grafting: Prosthetic Graft Endothelial Cell Seeding and Gene Therapy. *Microsurgery* 18:263-256) due most likely to the fact the cells did not adhere properly to the graft and/or lost their EC function due to ex-vivo manipulation.

Endothelial cell growth factors and environmental conditions in situ are therefore essential in modulating endothelial cell adherence, growth and differentiation at the site of blood vessel injury. Accordingly, with respect to restenosis and other blood vessel diseases, there is a need for the development of new methods and compositions for coating medical devices, including stents and synthetic grafts, which would promote and accelerate the formation of a functional endothelium on the surface of implanted devices so that a confluent EC monolayer is formed on the target blood vessel segment or grafted lumen and thereby inhibiting neo-intimal hyperplasia.

Systemic administration of drugs to prevent diseases such as restenosis has not been effective due to the nature of the disease, and the properties of the drug used, for example, drug solubility, in vivo stability of the drug, bioavailability of the drug, etc. Upon systemic administration, the drug is conveyed by the circulating blood and distributed into body areas including normal tissues. At diseased sites, the drug concentration is first low and ineffective which frequently increases to toxic levels, while in non-diseased areas, the presence of the drug causes undesired side effects. In certain instances, drugs are readily susceptible to metabolic degradation after being administered before they reach target sites. Therefore, drug dose is often increased to achieve pharmacological efficacy and prolong duration, which causes increased systemic burden to normal tissues as well as cost concern for the patient. In other instances, the therapeutic potential of some potent drugs cannot be fulfilled due to their toxic side effects.

Local drug delivery vehicles such as drug eluting stents (DES) have been developed. See U.S. Pat. No. 6,273,913, U.S. Pat. No. 6,258,121, and U.S. Pat. No. 6,231,600.

However, drug eluting stents of the prior art are limited by many factors such as, the type of drug, the amount of drug to be released and the amount of time it takes to release the drug. Other factors which need to be considered in regards to drug eluting stents are the drug interactions with other stent coating components, such as polymer matrices, and individual drug properties including hydrophobicity, molecular weight, intactness and activity after sterilization, as well as efficacy of drug delivery and toxicity of the drugs used. With respect to polymer matrices of drug eluting stents, one must consider the polymer type, polymer ratio, drug loading capability, and biocompatibility of the polymer and the drug-polymer compatibility such as drug pharmacokinetics.

Additionally, the drug dose in a drug eluting stent is pre-loaded and an adjustment of drug dose upon individual conditions and need cannot be achieved with accuracy. In regard to drug release time, drug eluting stents instantly start to release the drug upon implantation and an ideal real-time release cannot be achieved.

U.S. Pat. Nos. 5,288,711; 5,563,146; 5,516,781, and 5,646,160 disclose a method of treating hyperproliferative vascular disease with rapamycin alone or in combination with mycophenolic acid. The rapamycin is given to the patient by various methods including, orally, parenterally, intravascular, intranasally, intrabronchially, transdermally, rectally, etc. The patents further disclose that the rapamycin can be provided to the patient via a vascular stent, which is impregnated with the rapamycin alone or in combination with heparin or mycophenolic acid. One of the problems encountered with the impregnated stent of the patents is that the drug is released immediately upon contact with the tissue and does not last for the amount of time required to prevent restenosis.

European Patent Application No. EP 0 950 386 discloses a stent with local rapamycin delivery, in which the rapamycin is delivered to the tissues directly from micropores in the stent body, or the rapamycin is mixed or bound to a polymer coating applied on the stent. EP 0 950 386 further discloses that the polymer coating consists of purely nonabsorbable polymers such as polydimethylsiloxane, poly(ethylene-vinylacetate), acrylate based polymers or copolymers, etc. Since the polymers are purely nonabsorbable, after the drug is delivered to the tissues, the polymers remain at the site of implantation which may stimulate an inflammatory response. Nonabsorbable polymers remaining in large amounts adjacent to the tissues have been, however, known to induce inflammatory reactions on their own with restenosis recurring at the implantation site thereafter.

Additionally, U.S. Pat. No. 5,997,517 discloses a medical device coated with a thick coherent bond coat of acrylics, epoxies, acetals, ethylene copolymers, vinyl polymers and polymers containing reactive groups. The polymers disclosed in the patent are also nonabsorbable and can cause side effects when used in implantable medical devices similarly as discussed above with respect to EP 0 950 386.

An increase in the circumference of the artery (outward or positive remodeling) can partially or totally compensate for the encroachment of the lumen caused by the formation of atherosclerotic plaques or by intimal hyperplasia after arterial injury. However, the arterial wall may also respond with constrictive (negative) remodeling, thereby aggravating the luminal narrowing response. It has been recognized that the geometric change in arterial size and plaque area may equally contribute to the luminal narrowing in atherosclerotic disease. Current invasive strategies for the treatment of CAD or restenosis have focused on the reduction of the atherosclerotic or neointimal burden or vessel bypass and have neglected the remodeling process. In many instances these standard approaches are not possible because of the severity or extent of the disease process. It is estimated that between 5 and 20% of patients undergoing coronary angiography have diffuse proximal and distal coronary disease that is not amenable to conventional revascularization techniques.

As described above, one of the aforementioned approaches has significantly reduced the incidence of thrombosis or restenosis over an extended period of time. More recently and in certain cases studies have shown that drug eluting stents may be associated with fatal thrombosis after they have been implanted into patients for a period of several years due to the absence of or disfunctional endothelium, Additionally, the coating of prior art medical devices have been shown to crack upon implantation of the devices. It is therefore a long-felt need to develop an efficient system for reestablishing a functional endothelium at the site of blood vessel injury as well as a local drug delivery system to overcome limitations of current available techniques.

SUMMARY OF INVENTION

The invention provides a medical device for implanting into the lumen of a blood vessel or an organ with a lumen, which device provides a biocompatible system for the delivery of therapeutic agents locally in a safe and controlled manner. The medical device additionally can induce the formation of a functional endothelium at the site of injury, thereby stimulating positive blood vessel remodeling.

The implantable medical device comprises a coating comprising a biocompatible matrix, which can be made of a composition for extended or controlled delivery of a pharmaceutical substance to adjacent tissue. The coating on the medical device further comprises one or more ligands for capturing target cells on its luminal surface, for example, native/normal or genetically modified target cells which secrete a desired pharmaceutical substance constitutively or when stimulated to do so. For example, circulating progenitor endothelial cells can be the target cells which can be captured and immobilized on the luminal or blood contacting surface of the device to restore, enhance or accelerate the formation of a functional endothelium at the site of implantation of the device due to blood vessel injury.

In one embodiment, the medical device comprises, for example, a stent, a synthetic vascular graft or a catheter having a structure adapted for the introduction into a patient. For example, in the embodiments wherein the medical device is a stent or graft, the device is operably configured to have a luminal or blood contacting surface and an outer or abluminal surface which is adapted for contacting adjacent tissue when inserted into a patient.

The medical device of the invention can be any device that is implantable into a patient. For example, in one embodiment the device is for insertion into the lumen of a blood vessels or a hollowed organ, such as stents, stent grafts, heart valves, catheters, vascular prosthetic filters, artificial heart, external and internal left ventricular assist devices (LVADs), and synthetic vascular grafts, for the treatment of diseases such as cancer, vascular diseases, including, restenosis, artherosclerosis, thrombosis, blood vessel obstruction, or any other applications additionally covered by these devices.

The medical device of the invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port. The medical device can be made of numerous materials depending on the device. For example, a stent of the invention can be made of stainless steel, Nitinol (NiTi), or chromium alloy and biodegradable materials. Synthetic vascular grafts can be made of a cross-linked PVA hydrogel, polytetrafluoroethylene (PTFE), expanded polytetrafluoroethylene (ePTFE), porous high density polyethylene (HOPE), polyurethane, and polyethylene terephthalate, or biodegradable materials such as polylactide polymers and polyglycolide polymers or copolymers thereof.

In one embodiment, the medical device comprises a coating comprising a matrix which comprises a nontoxic, biocompatible, bioerodible and biodegradable synthetic material. The coating may further comprise one or more pharmaceutical substances or drug compositions for delivering to the tissues adjacent to the site of implantation, and one or more ligands, such as peptides which bind to cell surface receptors, small and/or large molecules, and/or antibodies or combinations thereof for capturing and immobilizing, in particular progenitor endothelial cells on the blood contacting surface of the medical device.

In one embodiment, the implantable medical device comprises a stent. The stent can be selected from uncoated stents available in the art. In accordance with one embodiment, the stent is an expandable intraluminal endoprosthesis comprising a tubular member as described in U.S. Pat. No. 6,117,165, which relevant disclosure is incorporated herein by reference. In another embodiment, the stent is made of a biodegradable material.

In one embodiment, the controlled-release matrix can comprise one or more polymers and/or oligomers from various types and sources, including, natural or synthetic polymers, which are biocompatible, biodegradable, bioabsorbable and useful for controlled-released of the medicament. For example, in one embodiment, the naturally occurring polymeric materials can include proteins such as collagen, fibrin, tropoelastin, elastin, cross-linked tropoelastin and extracellular matrix component, or other biologic agents or mixtures thereof. In this embodiment of the invention, the naturally-occurring material can be made by genetic engineering techniques from exogenous genes carried by vectors, such as a plasmid vector and engineered into a host, such as a bacterium. In this embodiment, desired polymer proteins such as tropoelastin and elastin can be produced and isolated for use in the matrix. In alternate embodiments, the naturally occurring polymeric matrices can be purified from natural sources by known methods or they can be obtained by chemical synthesis of the protein polymer. In certain embodiments, the naturally occurring material can be chemically modified or synthesized, for example, by cross-linking the material such as proteins, or by methylation, phosphorylation and the like. In another embodiment, the matrix can comprise a denuded blood vessel or blood vessel scaffolds and/or components thereof.

In one embodiment, the matrix may comprise a synthetic material which can include polyesters such as polylactic acid, polyglycolic acid or copolymers and or combinations thereof, a polyanhydride polycaprolactone, polyhydroxybutyrate valerate, and other biodegradable polymer, or mixtures or copolymers thereof. In this embodiment, the matrix comprises poly(lactide-coglycolide) as the matrix polymer for coating the medical device. In this embodiment, the poly(lactide-co-glycolide) composition comprises at least one polymer of poly-DL-co-glycolide or copolymer or mixtures thereof, and it is mixed together with the pharmaceutical substances to be delivered to the tissues. The coating composition is then applied to the surface of the device using standard techniques such as spraying, dipping, and/or chemical vaporization. Alternatively, the poly(lactide-co-glycolide) (PGLA) solution can be applied as a single layer separating a layer or layers of the pharmaceutical substance(s).

In another embodiment, the coating composition further comprises pharmaceutically acceptable polymers and/or pharmaceutically acceptable carriers, for example, nonabsorbable polymers, such as ethylene vinyl acetate (EVAC) and methylmethacrylate (MMA). The nonabsorbable polymer, for example, can aid in further controlling release of the substance by increasing the molecular weight of the composition thereby delaying or slowing the rate of release of the pharmaceutical substance.

In certain embodiments, the polymer material or mixture of various polymers can be applied together as a composition with the pharmaceutical substance on the surface of the medical device and can comprise a single layer. Multiple layers of composition can be applied to form the coating. In another embodiment, multiple layers of polymer material or mixtures thereof can be applied between layers of the pharmaceutical substance. For example, the layers may be applied sequentially, with the first layer directly in contact with the uncoated surface of the device and a second layer comprising the pharmaceutical substance and having one surface in contact with the first layer and the opposite surface in contact with a third layer of polymer which is in contact with the surrounding tissue. Additional layers of the polymer material and drug composition can be added as required, alternating each component or mixtures of components thereof.

In another embodiment, the matrix may comprise non-polymeric materials such as nanoparticles formed of, for example, metallic alloys or other materials. In this embodiment, the coating on the medical device can be porous and the pharmaceutical substances can be trapped within and between the particles. In this embodiment, the size of the particles can be varied to control to the rate of release of the pharmaceutical substance trapped in the particles depending on the need of the patient. In one embodiment, the pharmaceutical composition can be a slow/controlled-release pharmaceutical composition.

Alternatively, the pharmaceutical substance can be applied as multiple layers of a composition and each layer can comprise one or more drugs surrounded by polymer material. In this embodiment, the multiple layers of pharmaceutical substance can comprise a pharmaceutical composition comprising multiple layers of a single drug; one or more drugs in each layer, and/or differing drug compositions in alternating layers applied. In one embodiment, the layers comprising pharmaceutical substance can be separated from one another by a layer of polymer material. In another embodiment, a layer of pharmaceutical composition may be provided to the device for immediate release of the pharmaceutical substance after implantation.

In one embodiment, the pharmaceutical substance or composition may comprise one or more drugs or substances which can inhibit smooth muscle cell migration and proliferation at the site of implantation, can inhibit thrombus formation, can promote endothelial cell growth and differentiation, and/or can inhibit restenosis after implantation of the medical device. Additionally, the capturing of the progenitor endothelial cells on the luminal surface of the medical device accelerates the formation of a functional endothelium at the site of injury.

Examples of compounds or pharmaceutical compositions which can be incorporated in the matrix, include, but are not limited to prostacyclin, prostacyclin analogs, α-CGRP, α-CGRP analogs or α-CGRP receptor agonists; prazosin; monocyte chemoattractant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosglitazone; nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like. The aforementioned compounds and pharmaceutical substances can be applied to the coating on the device alone or in combinations and/or mixtures thereof.

In one embodiment, the implantable medical device can comprise a coating comprising one or more barrier layers in between said one or more layers of matrix comprising said pharmaceutical substances. In this embodiment, the barrier layer may comprise a suitable biodegradable material, including but not limited to suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), polylactic acid-co-glycolic acid), 50/50 (DL-lactide-co-glycolide); polydioxanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the coating on a device may have depends on the amount of therapeutic needed as dictated by the therapy required by the patient. For example, the longer the treatment, the more therapeutic substance required over a period of time, the more barrier layers to provide the pharmaceutical substance in a timely manner.

In one embodiment, the ligand is applied to the blood contacting surface of the medical device and the ligand specifically recognizes and binds a desired component or epitope on the surface of target cells in the circulating blood. In one embodiment, the ligand is specifically designed to recognize and bind only the genetically-altered mammalian cell by recognizing only the genetically-engineered marker molecule on the cell membrane of the genetically-altered cells. The binding of the target cells immobilizes the cells on the surface of the device.

In alternate embodiment, the ligand on the surface of the medical device for binding the genetically-altered cell is selected depending on the genetically engineered cell membrane marker molecule. That is, the ligand binds only to the cell membrane marker molecule or antigen which is expressed by the cell from extrachromosomal genetic material provided to the cell so that only the genetically-modified cells can be recognized by the ligand on the surface of the medical device. In this manner, only the genetically-modified cells can bind to the surface of the medical device. For example, if the mammalian cell is an endothelial cell, the ligand can be at least one type of antibody, antibody fragments or combinations thereof; the antibody is specifically raised against a specific target epitope or marker molecule on the surface of the target cell. In this aspect of the invention, the antibody can be a monoclonal antibody, a polyclonal antibody, a chimeric antibody, or a humanized antibody which recognizes and binds only to the genetically-altered endothelial cell by interacting with the surface marker molecule and, thereby modulating the adherence of the cells onto the surface of the medical device. The antibody or antibody fragment of the invention can be covalently or noncovalently attached to the surface of the matrix, or tethered covalently by a linker molecule to the outermost layer of the matrix coating the medical device. In this embodiment, for example, the monoclonal antibodies can further comprises Fab or F(ab')$_2$ fragments. The antibody fragment of the invention comprises any fragment size, such as large and small molecules which retain the characteristic to recognize and bind the target antigen as the antibody.

In another embodiment, the antibody or antibody fragment of the invention recognize and bind antigens with specificity for the mammal being treated and their specificity is not dependent on cell lineage. In one embodiment, for example, in treating restenosis wherein the cells may not be genetically modified to contain specific cell membrane marker molecules, the antibody or fragment is specific for selecting and binding circulating progenitor endothelial cell surface antigen such as CD133, CD34, CD14, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, MI-IC such as H-2K$^k$ and HLA-DR antigen.

In another embodiment, the coating of the medical device comprises at least one layer of a biocompatible matrix as described above, the matrix comprises an outer surface for attaching a therapeutically effective amount of at least one type of small molecule of natural or synthetic origin. The small molecule recognizes and interacts with, for example, progenitor endothelial cells in the treatment of restenosis, to immobilize the cells on the surface of the device to form an endothelial layer. The small molecules can be used in conjunction with the medical device for the treatment of various diseases, and can be derived from a variety of sources such as cellular components such as fatty acids, proteins, nucleic acids, saccharides and the like and can interact with an antigen on the surface of a progenitor endothelial cell with the same results or effects as an antibody. In this aspect of the invention, the coating on the medical device can further comprise a compound such as a growth factor as described herewith in conjunction with the coating comprising an antibody or antibody fragment.

In another embodiment, the coating of the medical device comprises at least one layer of a biocompatible matrix as described above, the matrix comprising a luminal surface for attaching a therapeutically effective amount of at least one type of small molecule of natural or synthetic origin. The small molecule recognizes and interacts with an antigen on the target cell such as a progenitor endothelial cell surface to immobilize the progenitor endothelial cell on the surface of the device to form endothelium. The small molecules can be derived from a variety of sources such as cellular components including, fatty acids, peptides, proteins, nucleic acids, saccharides and the like and can interact, for example, with a structure such as an antigen on the surface of a progenitor endothelial cell with the same results or effects as an antibody.

In another embodiment, there is provided a method for treating vascular disease such as restenosis and artherosclerosis, comprising administering a pharmaceutical substance locally to a patient in need of such substance. The method comprises implanting into a vessel or hollowed organ of a patient a medical device with a coating, which coating comprises a pharmaceutical composition comprising a drug or substance for inhibiting smooth muscle cell migration and thereby restenosis, and a biocompatible, biodegradable, bioerodible, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

In another embodiment, there is provided a method of making a coated medical device or a medical device with a coating, which comprises applying to a surface of a medical device a polymer or non-polymer matrix and a pharmaceutical composition comprising one or more drugs, and applying a ligand to the medical device so that the ligand attaches to a surface of the device and is designed to bind molecules on the cell membrane of circulating native or genetically engineered cells. In this embodiment, the polymer matrix comprises a biocompatible, biodegradable, nontoxic polymer matrix such as collagen, tropocollagen, elastin, tropoelastin, cross-linked tropoelastin, poly(lactide-co-glycolide) copolymer, and one or more pharmaceutical substances, wherein the matrix and the substance(s) can be mixed prior to applying to the medical device. In this embodiment, at least one type of ligand is applied to the surface of the device and can be added on top or on the outer surface of the device with the drug/matrix composition in contact with the device surface. The method may alternatively comprise the step of applying at least one layer of a pharmaceutical composition comprising one or more drugs and pharmaceutically acceptable carriers, and applying at least one layer of a polymer matrix to the medical device.

In one embodiment, the matrix can be applied with or without the pharmaceutical substance, and the ligand can be applied independently to the medical device by several methods using standard techniques, such as dipping, spraying or vapor deposition. In an alternate embodiment, the polymer matrix can be applied to the device with or without the pharmaceutical substance. In this aspect of the invention wherein a polymer matrix is applied without the drug, the drug can be applied as a layer between layers of matrices. In other embodiments, a barrier layer is applied between the layers comprising the pharmaceutical substances.

In one embodiment, the method comprises applying the pharmaceutical composition as multiple layers with the ligand applied on the outermost surface of the medical device so that the ligand such as antibodies can be attached in the luminal surface of the device. In one embodiment, the method for coating the medical device comprises: applying to a surface of said medical device at least one or more layers of a matrix, one or more pharmaceutical substance(s), and a basement membrane component; applying to said at least one layer of said composition on said medical device a solution comprising at least one type of ligand for binding and immobilizing genetically-modified target cells; and drying said coating on the stent under vacuum at low temperatures.

In another embodiment, the coating is comprised of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α ligands, tissue plasminogen activator, statins such as atorvastatin, erythropoietin, darbepotin, serine proteinase-1 (SERP-1) and pravastatin, steroids, and/or antibiotics.

In another embodiment, there is provided a therapeutic, drug delivery system and method for treating diseases in a patient. The therapeutic or drug delivery system comprises a medical device with a coating composed of a matrix comprising at least one type of ligand for recognizing and binding target cells such as progenitor endothelial cells or genetically-altered mammalian cells and genetically-altered mammalian cells which have been at least singly or dually-transfected.

In one embodiment, the coating on the present medical device comprises a biocompatible matrix and at least one type of pharmaceutical substance or ligand, which specifically recognize and bind target cells such as progenitor endothelial cells such as in the prevention or treatment of restenosis, or genetically-altered mammalian cells, onto the surface of the device, such as in the treatment of blood vessel remodeling and cancer.

Additionally, the coating of the medical device may optionally comprise at least an activating compound for regulating the expression and secretion of the engineered genes of the genetically-altered cells. Examples of activator stimulatory compounds, include but is not limited to chemical moieties, and peptides, such as growth factors. In embodiments when the coating comprises at least one compound, the stimulus, activator molecule or compound may function to stimulate the cells to express and/or secrete at least one therapeutic substance for the treatment of disease.

In one embodiment, the coating on the medical device comprises a biocompatible matrix which comprises an outer surface for attaching a therapeutically effective amount of at least one type of ligand such as an antibody, antibody fragment, or a combination of the antibody and the antibody fragment, or at least one type of molecule for binding the engineered marker on the surface of the genetically-modified cell. The present antibody or antibody fragment recognizes and binds an antigen or the specific genetically-engineered cell surface marker on the cell membrane or surface of target cells so that the cells are immobilized on the surface of the device. In one embodiment, the coating may optionally comprise an effective amount of at least one compound for stimulating the immobilized progenitor endothelial cells to either accelerate the formation of a mature, functional endothelium if the target cells are circulating progenitor cells, or to stimulate the bound cells to express and secrete the desired gene products if the target are genetically-altered cells on the surface of the medical device.

In one embodiment, the compound of the coating of the invention, for example in treating restenosis, comprises any compound which stimulates or accelerates the growth and differentiation of the progenitor cell into mature, functional endothelial cells. In another embodiment, the compound is for stimulating the genetically modified cells to express and secrete the desired gene product. For example, a compound for use in the invention may be a growth factor such as vascular endothelial growth factor (VEGF), basic fibroblast growth factor, platelet-induced growth factor, transforming growth factor beta 1, acidic fibroblast growth factor, osteonectin, angiopoietin 1 (Ang-1), angiopoietin 2 (Ang-2), insulin-like growth factor, granulocyte-macrophage colony-stimulating factor, platelet-derived growth factor AA, platelet-derived growth factor BB, platelet-derived growth factor AB and endothelial PAS protein 1.

In another embodiment, for example when using genetically-altered mammalian cells, the activating agents or compounds useful for stimulating the cells to express and secrete the genetically-engineered gene products include, but are not limited to estrogen, tetracycline and other antibiotics, tamoxiphen, etc., and can be provided to the patient via various routes of administration, such as through the skin via a patch and subcutaneously.

The invention also provides methods for treating a variety of diseases, such as vascular disease, cancer, blood vessel remodeling, severe coronary artery disease. artherosclerosis, restenosis, thrombosis, aneurysm and blood vessel obstruction. In one embodiment, there is provided a method for retaining or sealing the medical device insert to the vessel wall, such as a stent or synthetic vascular graft, heart valve, abdominal aortic aneurysm devices and components thereof, and for establishing vascular homeostasis, thereby preventing excessive intimal hyperplasia as in restenosis. In the present method of treating atherosclerosis, the artery may be either a coronary artery or a peripheral artery such as the femoral artery. Veins can also be treated using these techniques and medical device.

With respect to the treatment of restenosis, the invention also provides an engineered method for inducing a healing response. In one embodiment, a method is provided for rapidly inducing the formation of a confluent layer of endothelium in the luminal surface of an implanted device in a target lesion of an implanted vessel, in which the endothelial cells express nitric oxide synthase and other anti-inflammatory and inflammation-modulating factors. The invention also provides a medical device which has increased biocompatibility over prior art devices, and decreases or inhibits tissue-based excessive intimal hyperplasia and restenosis by decreasing or inhibiting smooth muscle cell migration, smooth muscle cell differentiation, and collagen deposition along the inner luminal surface at the site of implantation of the medical device.

In an embodiment, a method for coating a medical device comprises the steps of: applying at least one layer of a biocompatible matrix to the surface of the medical device, wherein the biocompatible matrix comprises at least one component selected from the group consisting of a polyurethane, a segmented polyurethane-urea/heparin, a poly-L-lactic acid, a cellulose ester, a polyethylene glycol, a polyvinyl acetate, a dextran, gelatin, collagen, elastin, tropoelastin, laminin, fibronectin, vitronectin, heparin, fibrin, cellulose and carbon and fullerene, and applying to the biocompatible matrix, simultaneously or sequentially, a therapeutically effective amounts of at least one type of antibody, antibody fragment or a combination thereof, and at least one compound which stimulates endothelial cell growth and differentiation.

The invention further provides a method for treating vascular disease in a mammal comprising implanting a medical device into the lumen of a vessel or tubular organ of the mammal, wherein the medical device is coated with (a) a biocompatible matrix, (b) therapeutically effective amounts of at least one type of antibody, antibody fragment or a combination thereof, and (c) at least one compound; wherein the antibody or antibody fragment recognizes and binds an antigen on a progenitor endothelial cell surface so that the progenitor endothelial cell is immobilized on the surface of the matrix, and the compound is for stimulating the immobilized progenitor endothelial cells to form an endothelium on the surface of the medical device.

In one embodiment, a therapeutic/drug delivery system for treating a disease in a patient is also provided. The therapeutic or drug delivery system comprises genetically-altered mammalian cells, comprising exogenous nucleic acid encoding a genetically-engineered cell membrane marker and at least one therapeutic gene product, and a medical device for implantation into a patient. In one embodiment, the genetic engineered cells are transfected in vitro with an appropriate transfection vector comprising the exogenous genetic material for providing the desired genes to the cells. In this embodiment, the cells can be any mammalian cell, either autologous, allogenic or xenogenic, such as endothelial cells, fibroblasts, myoblasts and the like. In this embodiment, the medical device is coated with a biocompatible matrix comprising a ligand which binds only to the genetically-altered mammalian cells by way of binding the genetically-engineered cell membrane marker molecule or antigen on the surface of the cells.

In the therapeutic and/or drug delivery system of this embodiment, the genetically-altered cells are provided with exogenous genetic material to introduce at least one desired gene which encodes a cell surface marker molecule or antigen and at least one gene which encodes a therapeutic gene product. The system optionally comprises a signal system, such as an activating compound or molecule for stimulating the genetically-altered mammalian cells to express and/or secrete the desired gene product and/or the marker gene.

Thus, in one embodiment, the exogenous genetic material for introducing into mammalian cells is engineered to encode a cell membrane marker which specifically binds to the ligand on the device. For example, if the device is for implantation in a blood vessel lumen, the exogenous genetic material encodes a cell membrane marker not found in any cell circulating in the blood stream, other than the genetically-engineered cells provided to the patient.

There is also provided a coated medical devices and methods for the treatment of a variety of diseases such as vascular disease including but not limited to atherosclerosis, cancer, and rheumatoid arthritis. The medical device of the invention comprises a coating for the specific in vivo capturing and immobilization of genetically-altered mammalian cells which are introduced, simultaneously or sequentially, into the patient upon implantation of the coated medical device.

There is also provided immobilized genetically-altered cells which express and/or secrete at least one type of substance or therapeutic agent for the treatment of a specific disease. In this aspect of the invention, for example in the treatment of cancer, the cells, e.g., endothelial cells are genetically-altered by introducing exogenous genetic material into the cells. In one embodiment, the genetic material is introduced into the nucleus of the cells and is DNA, such as extrachromosomal DNA. The extrachromosomal DNA may be a vector such as an adenoviral vector, a plasmid such as a naked plasmid, linear or short DNA, and the like. In one embodiment, the DNA comprises a regulatory/expression cassette for controlling the expression of the desired marker and/or therapeutic genes. In one embodiment, the regulatory cassette may comprise regulatory elements for constitutive expression of the therapeutic genes or may comprise elements that can be controlled or expressed as needed by the patient.

In one embodiment, the medical device for implantation into the patient comprises a coating; wherein the coating comprises a matrix bearing at least one type of ligand, which recognizes and binds genetically-altered target cells. In this embodiment, the ligand only recognizes and binds to a specific cell membrane marker molecule or antigen which is engineered into the cells. Thus in this embodiment, such ligand only recognizes the genetically-altered mammalian cells introduced into the patient, and the genetically-altered mammalian cells bind to said medical device and express and secrete the marker molecule or antigen as well as at least one therapeutic gene product.

In another embodiment, the therapeutic or drug delivery system may further comprise an activating molecule for stimulating said genetically-altered mammalian cells to express and/or secrete the desired therapeutic gene products. In this aspect of the invention, a compound such as a chemical stimulus or a peptide can be provided to the patient by several methods, including, oral route, a thermal or dermal patch, intravenously, intradermally and the like. In this embodiment, the genetically-altered mammalian cells may be autogenic or xenogenic, such as mature endothelial cells, fibroblasts, muscle cells, epithelial cells, etc. and comprise exogenous nucleic acid which can be extrachromosomal DNA. In one embodiment, the DNA is provided in the form of a vector, such as an adenovirus vector, naked plasmid DNA, linear DNA and the like. In one embodiment, the extrachromosomal DNA comprises a regulatory cassette, a gene which encodes a cell membrane antigen and at least one gene which encodes a peptide for treating a disease. In one aspect of this embodiment, the cell membrane specific gene encodes, for example, an osteogenic or a prostatic cell membrane protein.

In one embodiment, the extrachromosomal genetic material comprises a nucleic acid sequence which encodes the therapeutic/drug product, such as plasminogen activator, vascular endothelial growth factor and angiogenin for use in blood vessel remodeling, or anti-angiogenic factor in the treatment of for example, cancer.

In another embodiment, a method for treating disease in a patient is provided. The method comprises:
  providing genetically-altered mammalian cells to the patient; comprising an exogenous nucleic acid encoding a genetically-engineered cell membrane marker molecule and at least one therapeutic gene product;
  implanting a medical device comprising a coating into the patient; the coating comprising a matrix bearing at least one ligand, wherein the ligand recognizes and binds the genetically-engineered cell membrane marker molecule on the genetically-altered mammalian cells, and wherein the genetically-altered mammalian cells bind to the medical device and contain genetic material to express and secrete the therapeutic gene product. In an embodiment of the invention, the therapeutic gene and gene product comprises, for example, vascular endothelial growth factor, angiogenin, anti-angiogenic factor, and fibroblast growth factor.

The invention also provides a method for treating disease in a patient, the method comprises: providing genetically-altered mammalian cells to the patient; implanting a medical device into the patient; wherein the medical device comprises a coating which comprises a matrix bearing at least one ligand, wherein the ligand specifically recognizes and binds at least one marker molecule such as a receptor on the genetically-altered mammalian cells, and wherein the genetically-altered mammalian cells bind to the medical device and comprise exogenous nucleic acid for expressing and secreting a therapeutic gene product.

In another embodiment, a method for recruiting cells to a blood contacting surface in viva is provided. The method comprises implanting a medical device into a blood vessel of a subject, said blood vessel implant having a blood contacting surface configured to bind target cells circulating in the blood stream of the subject; wherein the target cells attached to the blood contacting surface proliferate and form functional endothelium in situ or self-endothelialize the surface of the device in restoring normal endothelium at the site of blood vessel injury. The blood contacting surface can be a biodegradable scaffolding or can be coated with a biodegradable, biocompatible material. In this aspect of the invention, the biodegradable scaffolding when implanted into a blood vessel may undergo in situ degradation and the neo-endothelium formed on the luminal surface of the device restores the blood vessel continuity through the injured site so as to form a functional neo-vessel.

In an embodiment, there is provided a biodegradable scaffolding for forming an endothelialized vascular graft in situ, the scaffolding comprising: (a) a porous biodegradable support member having a lumen and an exterior surface; (b) the lumen surface comprising a first layer of at least one species of a polymeric compound coated to the support member, and wherein the compound is cross-linked to itself with a cross-linking agent that forms covalent bonds that are subject to enzymatic cleavage or non-enzymatic hydrolysis under in vivo conditions, and (c) a ligand with specific affinity for binding genetically-altered mammalian cells in vivo.

In another embodiment, a method for generating a self-endothelia zing graft in situ, the method comprising: (a) providing a prosthetic structure, having a surface exposed to circulating blood to a patient; (b) implanting the prosthetic structure into a subject or patient; (c) administering genetically-altered mammalian cells to the patient and (d) recruiting cells such as circulating genetically-altered mammalian cells from the blood to bind to the surface of the prosthetic structure to form a layer of genetically-altered cells on the surface of the prosthetic structure, which contain genes that can express and secrete a desirable gene product.

In yet another embodiment, a method is provided to promote in vivo vascular remodeling such as to increase the circumference of an artery by outward or positive remodeling to partially or totally compensate for the encroachment of the lumen caused by the formation of atherosclerotic plaques or by intimal hyperplasia after arterial injury so as to prevent or inhibit inward or negative remodeling of the injured vessel. In this embodiment, for example, a stent which is coated with a matrix and a ligand as described above in conjunction with genetically engineered cells, is provided for capturing genetically modified autologous cells such as endothelial progenitor cells, which are capable of secreting at least one potent anticoagulant and vasodilator such as prostacyclin, for example, prostaglandin I2, PGI2; calcitonin gene-related peptide such as α-CGRP; monocyte chemoattractant protein-1 (MCP-1) and the like. Other products which can be engineered to be produced by the cells include, nitric oxide (nitric oxide synthase gene), matrix metalloproteinases, acetylcholine, adenosine, 5-hydroxytryptamine, substance P, adrenomedulin, and the like. Any gene which product acts as or has vasodilator and/or anticoagulant properties can be used, for example, a vasodilator can cause the vascular smooth muscle relaxation. The gene encoding the vasodilator, for example, prostacyclin synthase gene can be provided to progenitor endothelial cells or endothelial cells by gene transfer technologies such as viral gene transfer using, for example, a cistronic gene construct, in the case of prostacyclin, for example, a cistronic cyclooxygenase-1/prostacyclin synthase gene construct can provide continuous delivery of prostacyclin locally. In this embodiment, the local delivery system for prostacyclin can be used to treat, for example, cerebral infarct and coronary blood vessel disease. Positive remodeling of blood vessels can also be used as therapy for regulating arteriogenesis, i.e., formation of mature blood vessels such as arterioles and arteries in adults, to form collateral blood vessels.

In another embodiment, suitable cells such as fibroblasts, endothelial cells, or progenitor endothelial cells can be transfected with a bicistronic vector encoding both a vasodilatory compound and a unique cell surface marker such as a truncated MHC-I, which can be recognized by a ligand such as an antibody immobilized on an intravascular prosthesis. For example, ligand such as an antibody, coated stent can be implanted into the coronary arteries of a patient, followed by transplantation of genetically modified cells such as genetically modified endothelial cells into the patient in need of treatment for vascular disease. In this embodiment and other embodiment using genetically modified cells, exogenous genes can be delivered into cells prior to transplantation of the cells using standard genetic engineering techniques using for example, a plasmid vector such as the bicistronic pMACSK$^K$.II plasmid vector (Miltenyi Biotec, Germany), which contains multiple cloning sites and wherein the gene of interest can be inserted, for example, prostacyclin synthase as well as a marker gene, such as the truncated MHC class I molecule, H-2K$^K$ as the selection marker for the mammalian cell lineage used.

In yet another embodiment, the exogenous gene delivery system for transfecting mammalian cells for use in therapy can comprise, for example, a lentivirus vector which may contain a truncated MHC class I antigen and vasodilator transgenes, for example, prostacyclin synthase and/or α-CGRP gene for treating vascular disease. In this embodiment, the mammalian cells to be transfected can be autologous endothelial cells, or endothelial progenitor cells, and the prosthetic device can be coated with ligands specific to the truncated MHC class 1 antigen such as and anti-H-2K$^k$ antibody.

BRIEF DESCRIPTION OF DRAWINGS

FIGS. 4A, 4B and 4C (cross-section) are schematic representations of an embodiment in which a stent strut comprises a ligand (outer) layer and a drug/polymer layer is applied in a section of the circumference of the strut and which appears as half circles in cross-section.

FIGS. 5A and 5B (cross-section) are schematic representations of an embodiment in which a stent strut comprises a ligand (outer) layer and a drug/polymer layer applied to a section of the circumference of the strut.

FIGS. 6A, 6B and 6C (cross-section) are schematic representations of an embodiment in which a stent strut comprises a ligand layer which is applied on the entire circumference of the strut and a drug/polymer layer is applied in dot matrix like pattern to a portion of the strut.

FIGS. 7A, 7B and 7C (cross-section) are schematic representations of an embodiment in which a stent strut comprises a drug/polymer layer surrounding the circumference of the strut and a ligand layer is applied on top of the drug/polymer layer, and an additional drug/polymer composition is applied on a portion of strut's surface in a dot matrix like pattern.

FIGS. 8A and 8B are schematic representations of alternate embodiments in which a stent strut comprises a ligand layer is applied to the entire circumference of the strut and a drug/polymer layer composition is applied on a portion of strut's surface in a dot matrix like pattern on top of the ligand layer (8A), and a drug/polymer matrix in a dot matrix like pattern is applied on the surface of the device and a ligand layer surrounding the entire circumference of the strut and covering the drug/polymer composition (8B).

FIGS. 9A, 9B and 9C (cross-section) are schematic representations of an embodiment in which a stent strut is shown in cross-section showing multiple layers of the coating including ligand (antibody) and drug/polymer components.

FIGS. 10A-1, 10A-2 and 10A-3 (cross-section) are schematic representations of an embodiment in which a stent strut is shown in cross-section showing multiple layers of the coating including intermediate and basement membrane layers on the surface of the strut.

FIG. 11 is a schematic representation of a stent partially coated to show the drug eluting composition and the ligand layer.

FIGS. 20A-2E are photomicrographs of HUVECs attached to dextran and anti-CD34 antibody (FIG. 20A); gelatin and anti-CD34 antibody (FIG. 20B); bare stainless steel disc (FIG. 20C); dextran-coated (FIG. 20D) and gelatin-coated (FIG. 20E) stainless steel disc which were incubated with HUVEC cell and stained with propidium iodide.

FIGS. 21A-21C are photomicrographs of a control stainless steel discs, coated with dextran without antibody. FIGS. 21D-21F are photomicrographs of control stainless steel discs coated with gelatin without antibody bound to its surface.

FIGS. 22A-22C are photomicrographs of stainless steel discs coated with dextran matrix with anti-CD34 antibody bound to its surface. FIGS. 22D-22F are photomicrographs of stainless steel discs coated with gelatin matrix with antibody bound to its surface.

FIG. 23A is an enlarged view of a section of the stent in FIG. 23A.

DETAILED DESCRIPTION

Figure 1A:
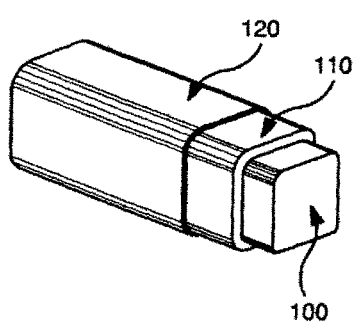
FIG. 1A is a schematic representation of an embodiment in which a stent strut comprises a coating surrounding the entire device and consisting of a ligand (outer) layer, a drug/polymer matrix (inner) layer surrounding the entire circumference of the strut.

In embodiments illustrated herein, there is provided a medical device in the form of an implantable structure, which is coated with a homogenous matrix comprising a pharmaceutical substance distributed in a biodegradable, biocompatible, non-toxic, bioerodible, or bioabsorbable polymer matrix, as described in U.S. application Ser. No. 10/442,669, which disclosure is incorporated herein by reference in its entirety, and a ligand such as an antibody or any other suitable molecule attached to the matrix for capturing and immobilizing circulating cells such as endothelial and progenitor endothelial cells on the luminal surface of the device. The medical device provides a mechanism for rapidly forming a functional endothelium at the site of implantation of the device, as described in pending U.S. Pat. No. 7,037,332 and U.S. application Ser. No. 10/360,567, which disclosures are incorporated herein by reference in their entirety. In one embodiment, the medical device can be a preserved blood vessel denuded or stripped of cells and can be from human, porcine or bovine origin. The preserved blood vessels form a scaffold suitable for, for example, as vascular graft segments.

The structure of the medical device has at least one surface where the matrix can be applied and comprises at least one or more base materials and it is for implanting into the lumen of an organ or a blood vessel. The base materials can be of various types, for example, stainless steel, Nitinol, MP35N, gold, tantalum, platinum or platinum iridium, or other biocompatible metals and/or alloys such as carbon or carbon fiber, cellulose acetate, cellulose nitrate, silicone, cross-linked polyvinyl acetate (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers, extracellular matrix components, proteins, collagen, fibrin or other bioactive agent, or mixtures thereof.

The medical device can be any device that is introduced temporarily or permanently into a mammal for the prophylaxis or therapy of a medical condition. These devices include any that are introduced subcutaneously, percutaneously or surgically to rest within an organ, tissue or lumen of an organ, such as arteries, veins, ventricles and/or atrium of the heart. Medical devices may include stents, stent grafts; covered stents such as those covered with polytetrafluoroethylene (PTFE), expanded polytetrafluoroethylene (ePTFE), or synthetic vascular grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., cross-linked PVA hydrogel), sensors, vascular sutures, vascular anastomosis fixtures, transmyocardial revascularization stents and/or other conduits.

The coating composition on the medical device comprises one or more pharmaceutical substances incorporated into a polymer matrix so that the pharmaceutical substance(s) is released locally into the adjacent or surrounding tissue in a slow or controlled-release manner and one or more ligands attached to the blood contacting surface of the medical device. The release of the pharmaceutical substance in a controlled manner allows for smaller amounts of drug or active agent to be released for a long period of time in a zero order elution profile manner. The release kinetics of a drug further depends on the hydrophobicity of the drug, i.e., the more hydrophobic the drug is, the slower the rate of release of the drug from the matrix. Alternative, hydrophilic drugs are released from the matrix at a faster rate. Therefore, the matrix composition can be altered according to the drug to be delivered in order to maintain the concentration of drug required at the implantation site for a longer period of time. There is, therefore, provided a long term effect of the drugs at the required site which may be more efficient in preventing restenosis and which may minimize the side effects of the released pharmaceutical substances used.

The matrix can comprise a variety of polymer or non-polymer materials. However, the matrix should be biocompatible, biodegradable, bioerodible, non-toxic, bioabsorbable, and with a slow rate of degradation. Biocompatible non-polymer matrices include, for example, those formed of nanoparticles made, for example, from metallic alloys. Such nanoparticles can be made of different sizes with various degrees of porosity to control the rate of release of pharmaceutical substances from the coating on the device. The nanoparticles can range in size from about 5 nm to about 5 µm in pore size and can have an average pore size of from about 40 nm to about 300 nm. The porous nanoparticles can be applied to the surface of the device and the pharmaceutical composition can be impregnated within the nanoparticles thereafter, follow by the application of the ligand.

Biocompatible polymer matrices that can be used in the invention include, but are not limited to, poly(lactide-co-glycolide), polyesters such as polylactic acid, polyglycolic acid or copolymers thereof, polyanhydride, polycaprolactone, polyhydroxybutyrate valerate, and other biodegradable polymer, or mixtures or copolymers, and the like. In another embodiment, the naturally occurring polymeric materials can be selected from proteins such as collagen, elastin, tropoelastin, cross-linked tropoelastin, fibrin, and extracellular matrix components, or other biologic agents or mixtures thereof.

Polymer matrices which can be used in the coating can include polymers such as poly(lactide-co-glycolide); poly-DL-lactide, poly-L-lactide, and/or mixtures thereof and can be of various inherent viscosities and molecular weights. For example, in one embodiment, poly(DL lactide-co-glycolide) (DLPLG, Birmingham Polymers Inc.) can be used. Poly(DL-lactide-co-glycolide) is a bioabsorbable, biocompatible, biodegradable, non-toxic, bioerodible material, which is a vinylic monomer and can serve as a polymeric colloidal drug carrier. The poly-DL-lactide material can be in the form of homogeneous composition and when solubilized and dried, it can form a lattice of channels in which pharmaceutical substances can be trapped for delivery to the tissues.

The drug release kinetics of the coating on the device can also be controlled depending on the inherent viscosity of the polymer or copolymer used as the matrix, and the amount of drug in the composition. The polymer or copolymer characteristics can vary depending on the inherent viscosity of the polymer or copolymer. For example, in one embodiment wherein poly(DL-lactide-co-glycolide) is used, the inherent viscosity can range from about 0.55 to about 0.75 (dL/g). Poly(DL-Lactide-co-Glycolide) can be added to the coating composition from about 50 to about 99% (w/w) of the polymeric composition. FIG. 1 is illustrative of a stent partially coated with the coating comprising poly(DL-lactide-co-glycolide) polymer matrix. The poly(DL-lactide-co-glycolide) polymer coating deforms without cracking, for example, when the coated medical device is subjected to stretch and/or elongation and undergoes plastic and/or elastic deformation. Therefore, polymers which can withstand plastic and elastic deformation such as poly(DL-lactide-co-glycolide) acid-based coats have advantageous characteristics over prior art polymers. Furthermore, the rate of dissolution of the matrix can also be controlled by using polymers of various molecular weight. For example, for slower rate of release of the pharmaceutical substances, the polymer should be of higher molecular weight. By varying the molecular weight of the polymer or combinations thereof, a preferred rate of dissolution can be achieved for a specific drug. Alternatively, the rate of release of pharmaceutical substances can be controlled by applying a polymer layer to the medical device, followed by one or more layers of drug(s), followed by one or more layers of the polymer. Additionally, polymer layers can be applied between drug layers to decrease the rate of release of the pharmaceutical substance from the coating.

The malleability of the coating composition can be further modified by varying the ratio of lactide to glycolide in the copolymer. For example, the ratio of components of the polymer can be adjusted to make the coating more malleable and to enhance the mechanical adherence of the coating to the surface of the medical device and aid in the release kinetics of the coating composition. In this embodiment, the polymer can vary in molecular weight depending on the rate of drug release desired. The ratio of lactide to glycolide can range, respectively, from about 50-85% to about 50-15% in the composition. By adjusting the amount of, for example, lactide in the polymer, the rate of release of the drugs from the coating can also be controlled.

The characteristic biodegradation of the polymer, therefore, can determine the rate of drug release from the coating. Information on the biodegradation of polymers can be obtained from the manufacturer information, for example, for lactides from Birmingham Polymers.

The principle mode of degradation, for example, for lactide and glycolide polymers and copolymers is hydrolysis. Degradation proceeds first by diffusion of water into the material followed by random hydrolysis, fragmentation of the material and finally a more extensive hydrolysis accompanied by phagocytosis, diffusion and metabolism. The hydrolysis of the material is affected by the size and hydrophilicity of the particular polymer, the crystallinity of the polymer and the pH and temperature of the environment.

In one embodiment, the degradation time may be shorter, for example, for low molecular weight polymers, more hydrophilic polymers, more amorphous polymers and copolymers higher in glycolide. Therefore at identical conditions, low molecular weight copolymers of DL-Lactide and Glycolide, such as 50/50 DL-PLG can degrade relatively rapidly whereas the higher molecular weight homopolymers such as L-PLA may degrade much more slowly.

Once the polymer is hydrolyzed, the products of hydrolysis are either metabolized or secreted. Lactic acid generated by the hydrolytic degradation of, for example, PLA can become incorporated into the tricarboxylic acid cycle and can be secreted as carbon dioxide and water. PGA can also be broken down by random hydrolysis accompanied by non-specific enzymatic hydrolysis to glycolic acid which can be either secreted or enzymatically converted to other metabolized species.

In another embodiment, the coating composition comprises a nonabsorbable polymer, such as ethylene vinyl acetate (EVAC), polybutyl-methacrylate (PBMA) and methylmethacrylate (MMA) in amounts from about 0.5 to about 99% of the final composition. The addition of EVAC, PBMA or methylmethacrylate can further increase malleability of the matrix so that the device can be more plastically deformable. The addition of methylmethacrylate to the coating can delay the degradation of the coat and therefore, can also improve the controlled release of the coat so that the pharmaceutical substance is released at even slower rates.

The coating of the medical device can be applied to the medical device using standard techniques to cover the entire surface of the device, or partially, as a single layer of a homogeneous mixture of drugs and matrix, or in a composition in a dot matrix pattern. In embodiments wherein the matrix and/or matrix/drug composition is applied as a single or multiple layers, the matrix or composition is applied in a thickness of from about 0 µm to about 150 µm; or from about 1 µm to about 100 µm. Alternative, multiple layers of the matrix/drug composition can be applied on the surface of the device in this thickness range. For example, multiple layers of various pharmaceutical substances can be deposited onto the surface of the medical device so that a particular drug can be released at one time, one drug in each layer, which can be separated by polymer matrix. The active ingredient or pharmaceutical substance component of the composition can range from about 1% to about 60% (w/w) or the composition. Upon contact of the coating composition with adjacent tissue where implanted, the coating can begin to degrade in a controlled manner. As the coating degrades, the drug is slowly released into adjacent tissue and the drug is eluted from the device so that the drug can have its effect locally. Additionally, since the polymers used with the device can form a lattice of channels, the drugs can be released slowly from the channels upon implantation of the device. The coated medical device provides an improved and local mechanism for delivering a drug to surrounding tissue without affecting the patient systemically. The drug elution via channels in the coating matrix and degradation of the matrix can be accomplished so that drug(s) can elute from the surface of the medical device once implanted for about a period from about one week to about one year. The drug may elute by erosion as well as diffusion when drug concentrations are low. With high concentrations of drug, the drug may elute via channels in the coating matrix.

The pharmaceutical substance of the invention includes drugs which are used in the treatment of vascular disease, such as artherosclerosis and restenosis. For example, the pharmaceutical substances include, but are not limited to antibiotics/antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodilators, thrombolytics, anti-metabolites, growth factor agonists, antimitotics, statins, steroids, steroidal and nonsteroidal anti-inflammatory agents, angiotensin converting enzyme (ACE) inhibitors, free radical scavengers, PPAR-gamma agonists, anti-cancer chemotherapeutic agents such as aromatase inhibitors. Some of the aforementioned pharmaceutical substances include, for example, cyclosporins A (CSA), rapamycin, rapamycin derivatives, mycophenolic acid (MPA), retinoic acid, n-butyric acid, butyric acid derivatives, vitamin E, probucol, L-arginine-L-glutamate, everolimus, sirolimus, biolimus, biolimus A-9, paclitaxel, puerarin, platelet factor 4, basic fibroblast growth factor (bFGF), fibronectin, simvastatin, fluvastatin, dihydroepiandrosterone (DHEA), and 17β-estradiol.

FIGS. 1-10 show schematic representation of various embodiments of the coating of the present medical device. The coating on the medical device comprising a biocompatible matrix for promoting the formation of a confluent layer of functional endothelial cells on the luminal surface of the device and pharmaceutical substances which inhibit excessive intimal smooth muscle cell hyperplasia, and thereby preventing restenosis and thrombosis. In one embodiment, the matrix comprises a synthetic or naturally-occurring material in which a therapeutically effective amount of at least one type of molecule such as an antibody that promotes adherence of endothelial, progenitor or stem cells to the medical device, and at least one compound such as a rapamycin, rapamycin derivatives, and/or estradiol for delivering to adjacent tissues. Upon implantation of the device, the cells that adhere to the surface of the device transform into a mature, confluent, functional layer of endothelium on the luminal surface of the medical device. The presence of a confluent layer of endothelial cells on the medical device can reduce the occurrence of restenosis and thrombosis at the site of implantation.

As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen of an organ, such as arteries, veins, ventricles or atrium of the heart. Medical devices may include stents, stent grafts, covered stents such as those covered with polytetrafluoroethylene (PTFE), expanded polytetrafluoroethylene (ePTFE), or synthetic vascular grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., cross-linked PVA hydrogel), vascular sutures, vascular anastomosis fixtures, transmyocardial revascularization stents and/or other conduits. In one embodiment, the stent can be made from a biodegradable material.

Coating of the medical device with the compositions and methods can stimulate the development of a confluent endothelial cell monolayer on the surface of the medical device as well as can modulate local chronic inflammatory response and other thromboembolic complications that result from blood vessel injury during implantation of the medical device.

As used herein, the term "antibody" refers to one type of antibody such as monoclonal, polyclonal, humanized, or chimeric antibody or a combination thereof, and wherein the monoclonal, polyclonal, humanized or chimeric antibody has high affinity and specificity for binding to one antigen or a functional equivalent of that antigen or other structure on the surface of the target cell. The term antibody fragment encompasses any fragment of an antibody such as Fab, F(ab')$_2$, and can be of any size, i.e., large or small molecules, which have the same results or effects as the antibody. (An antibody encompasses a plurality of individual antibody molecules equal to $6.022 \times 10^{23}$ molecules per mole of antibody).

In an aspect of the invention, a stent or synthetic graft of the invention is coated with a biocompatible, controlled-release matrix comprising antibodies that modulate adherence of circulating progenitor endothelial cells to the medical device. The antibodies of the invention recognize and bind with high affinity and specificity to progenitor endothelial cells surface antigens in the circulating blood so that the cells are immobilized on the surface of the device. In one embodiment, the antibodies comprise monoclonal antibodies reactive (recognize and bind) with progenitor endothelial cell surface antigens, or a progenitor or stem cell surface antigen, such as vascular endothelial growth factor receptor-1, -2 and -3 (VEGFR-1, VEGFR-2 and VEGFR-3 and VEGFR receptor family isoforms), Tie-1, Tie2, CD34, Thy-1, Thy-2, Muc-18 (CD146), 0030, stem cell antigen-1 (Sca-1), stem cell factor (SCF or c-Kit ligand), CD133 antigen, VE-cadherin, P1H12, TEK, CD31, Ang-1, Ang-2, or an antigen expressed on the surface of progenitor endothelial cells. In one embodiment, a single type of antibody that reacts with one antigen can be used. Alternatively, a plurality of different types of antibodies directed against different progenitor endothelial cell surface antigens can be mixed together and added to the matrix. In another embodiment, a cocktail of monoclonal antibodies is used to increase the rate of epithelium formation by targeting specific cell surface antigens. In this aspect of the invention, for example, anti-CD34 and anti-CD133 are used in combination and attached to the surface of the matrix on a stent or graft.

As used herein, a "therapeutically effective amount of the antibody" means the amount of an antibody that promotes adherence of endothelial, progenitor or stem cells to the medical device. The amount of an antibody needed to practice the invention varies with the nature of the antibody used. For example, the amount of an antibody used depends on the binding constant between the antibody and the antigen against which it reacts. It is well known to those of ordinary skill in the art how to determine therapeutically effective amounts of an antibody to use with a particular antigen.

As used herein, "intimal hyperplasia" is the undesirable increased in smooth muscle cell proliferation and matrix deposition in the vessel wall. As used herein "restenosis" refers to the reoccurrent narrowing of the blood vessel lumen. Vessels may become obstructed because of restenosis. After PTCA or PTA, smooth muscle cells from the media and adventitia, which are not normally present in the intima, proliferate and migrate to the intima and secrete proteins, forming an accumulation of smooth muscle cells and matrix protein within the intima. This accumulation causes a narrowing of the lumen of the artery, reducing blood flow distal to the narrowing. As used herein, "inhibition of restenosis" refers to the inhibition of migration and proliferation of smooth muscle cells accompanied by prevention of protein secretion so as to prevent restenosis and the complications arising therefrom.

The subjects that can be treated using the medical device, methods and compositions of this invention are mammals, and include a human, horse, dog, cat, pig, rodent, monkey and the like.

The term "progenitor endothelial cell" includes cells of any lineage that have the potential to differentiate into mature, functional endothelial cells. For example, the progenitor endothelial cells are endothelial cells at any developmental stage, from progenitor or stem cells to mature, functional epithelial cells from bone marrow, blood or local tissue origin and which are non-malignant, cells that are genetically-modified.

For in vitro studies or use of the coated medical device, fully differentiated endothelial cells may be isolated from an artery or vein such as a human umbilical vein, while progenitor endothelial cells are isolated from peripheral blood or bone marrow. The endothelial cells are bound to the medical devices by incubation of the endothelial cells with a medical device coated with the matrix that incorporates an antibody, a growth factor, or other agent that adheres to endothelial cells. In another embodiment, the endothelial cells can be transformed endothelial cells. The transfected endothelial cells contain vectors which express growth factors or proteins which inhibit thrombogenesis, smooth muscle cell migration, restenosis, or any other therapeutic end.

The methods of treatment of vascular disease illustrated herein can be practiced on any artery or vein. Included within the scope of this invention is atherosclerosis of any artery including coronary, infrainguinal, aortoiliac, subclavian, mesenteric and renal arteries. Other types of vessel obstructions, such as those resulting from a dissecting aneurysm are also encompassed by the invention.

The method of treating a mammal with vascular disease comprises implanting a coated medical device into the patient's organ or vessel, for example, in the case of a coated stent during angioplastic surgery. Once in situ, progenitor endothelial cells are captured on the surface of the coated stent by the recognition and binding of antigens on the progenitor cell surface by the antibody present on the coating. Once the progenitor cell is adhered to the matrix, the growth factor on the coating promotes the newly-bound progenitor endothelial cells to grow and differentiate and form a confluent, mature and functional endothelium on the luminal surface of the stent. Alternatively, the medical device is coated with the endothelial cells in vitro before implantation of the medical device using progenitor, stem cells, or mature endothelial cells isolated from the patient's blood, bone marrow, or blood vessel. In either case, the presence of endothelial cells on the luminal surface of the medical device inhibits or prevents excessive intimal hyperplasia and thrombosis.

Human umbilical vein endothelial cells (HUVEC) are obtained from umbilical cords according to the methods of Jaffe, et al., *J. Clin. Invest.*, 52:2745-2757, 1973, incorporated herein by reference and were used in the experiments. Briefly, cells are stripped from the blood vessel walls by treatment with collagenase and cultured in gelatin-coated tissue culture flasks in M199 medium containing 10% low endotoxin fetal calf serum, 90 ug/ml preservative-free porcine heparin, 20 ug/ml endothelial cell growth supplement (ECGS) and glutamine.

Progenitor endothelial cells (EPC) are isolated from human peripheral blood according to the methods of Asahara et al. (Isolation of putative progenitor endothelial cells for angiogenesis. *Science* 275:964-967, 1997, incorporated herein by reference). Magnetic beads coated with antibody to CD34 are incubated with fractionated human peripheral blood. After incubation, bound cells are eluted and can be cultured in EBM-2 culture medium. (Clonetics, San Diego, Calif.). Alternatively enriched medium isolation can be used to isolate these cells. Briefly, peripheral venous blood is taken from healthy male volunteers and the mononuclear cell fraction is isolated by density gradient centrifugation, and the cells are plated on fibronectin coated culture slides (Becton Dickinson) in EC basal medium-2 (EBM-2) (Clonetics) supplemented with 5% fetal bovine serum, human VEGF-A, human fibroblast growth factor-2, human epidermal growth factor, insulin-like growth factor-1, and ascorbic acid. EPCs are grown for 7-days, with culture media changes every 48 hours. Cells are characterized by fluorescent antibodies to CD133, CD45, CD34, CD31, VEGFR-2, Tie-2, and E-selectin.

As used herein "ligand" refers to a molecule that binds a cell membrane structure such as a receptor molecule on the circulating endothelial and/or progenitor cell. For example, the ligand can be an antibody, antibody fragment, small molecules such as peptides, cell adhesion molecule, basement membrane components, or combination thereof. In the embodiment using antibodies, the antibodies recognize and bind a specific epitope or structure, such as cell surface receptor on the cell membrane of the cell.

In one embodiment, the antibodies are monoclonal antibodies and may be produced according to the standard techniques of Kohler and Milstein (Continuous cultures of fused cells secreting antibody of predefined specificity. *Nature* 265:495-497, 1975, incorporated herein by reference), or can be obtained from commercial sources. Endothelial cells can be used as the immunogen to produce monoclonal antibodies directed against endothelial cell surface antigens.

In this aspect of the invention, the monoclonal antibodies directed against endothelial cells may be prepared by injecting HUVEC or purified progenitor endothelial cells into a mouse or rat. After a sufficient time, the mouse is sacrificed and spleen cells are obtained. The spleen cells are immortalized by fusing them with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity, i.e., reactivity with endothelial cell antigens.

Various techniques exist for enhancing yields of monoclonal antibodies such as injection of the hybridoma cells into the peritoneal cavity of a mammalian host which accepts the cells and then harvesting the ascites fluid. Where an insufficient amount of monoclonal antibody collects in the ascites fluid, the antibody is harvested from the blood of the host. Various conventional ways exist for isolation and purification of monoclonal antibodies so as to free the monoclonal antibodies from other proteins and other contaminants.

Also included within the scope of the invention are useful binding fragments of anti-endothelial cell monoclonal antibodies such as the Fab, F(ab')$_2$ of these monoclonal antibodies. The antibody fragments are obtained by conventional techniques. For example, useful binding fragments may be prepared by peptidase digestion of the antibody using papain or pepsin.

Antibodies of the invention are directed to an antibody of the IgG class from a murine source; however, this is not meant to be a limitation. The above antibody and those antibodies having functional equivalency with the above antibody, whether from a murine source, mammalian source including human, or other sources, or combinations thereof are included within the scope of this invention, as well as other classes such as IgM, IgA, IgE, and the like, including isotypes within such classes. In the case of antibodies, the term "functional equivalency" means that two different antibodies each bind to the same antigenic site on an antigen, in other words, the antibodies compete for binding to the same antigen. The antigen may be on the same or different molecule. In one embodiment, monoclonal antibodies reacting with high affinity and specificity to the endothelial cell surface antigen, for example CD133, CD45, CD34, CD31, CD14, CDw90, CD117, VEGFR-1, VEGFR-2, Muc-18 (CD146), CD130, stem cell antigen (Sca-1), stem cell factor 1 (SCF/c-Kit ligand), Tie-2, MHC such as H-2Kk and HLA-DR antigens are suitable as ligands.

CD34, and/or CD133 are used. Anti-CD34 monoclonal antibodies attached to a solid support have been shown to capture progenitor endothelial cells from human peripheral blood. After capture, these progenitor cells are capable of differentiating into endothelial cells. (Asahara et al. 1997. Isolation of putative progenitor endothelial cells for angiogenesis. *Science* 275:964-967.) Hybridomas producing monoclonal antibodies directed against CD34 can be obtained from the American Type Tissue Collection. (Rockville, Md.). In another embodiment, monoclonal antibodies reactive with endothelial cell surface antigens such as VEGFR-1 and VEGFR-2, CD133, or Tie-2 are used. In the embodiment using genetically-altered cell, antibodies are produced against the genetically engineered gene product using standard techniques in the same manner as described above, and then applied to the blood contacting surface of the medical device following matrix application.

Polyclonal antibodies reactive against endothelial cells isolated from the same species as the one receiving the medical device implant may also be used.

The term "stent" herein means any medical device which when inserted or implanted into the lumen of a vessel expands the cross-sectional lumen of a vessel. The term "stent" includes, but not limited to stainless steel stents, biodegradable stents commercially available which have been coated by the methods of the invention; covered stents such as those covered with PTFE or ePTFE. In one embodiment, this includes stents delivered percutaneously to treat coronary artery occlusions or to seal dissections or aneurysms of the splenic, carotid, iliac and popliteal vessels. In another embodiment, the stent is delivered into a venous vessel. The stent can be composed of polymeric or metallic structural elements onto which the matrix bioerodible, biodegradable, biocompatible polymer comprising the pharmaceutical substance and the ligand such as antibodies is applied, or the stent can be a composite of the matrix intermixed with a polymer. For example, a deformable metal wire stent can be used, such as that disclosed in U.S. Pat. No. 4,886,062 to Wiktor, incorporated herein by reference. A self-expanding stent of resilient polymeric material such as that disclosed in published international patent application WO91/12779 "Intraluminal Drug Eluting Prosthesis", incorporated herein by reference in its entirety, can also be used. Stents may also be manufactured using stainless steel, polymers, nickel-titanium, tantalum, gold, platinum-iridium, or Elgiloy and MP35N and other ferrous materials. Stents are delivered through the body lumen on a catheter to the treatment site where the stent is released from the catheter, allowing the stent to expand into direct contact with the lumenal wall of the vessel. In another embodiment, the stent comprises a biodegradable stent (H. Tamai, pp 297 in Handbook of Coronary Stents, 3rd Edition, Eds. P W Serruys and M J B Kutryk, Martin Dunitz (2000). It will be apparent to those skilled in the art that other self-expanding stent designs (such as resilient metal stent designs) could be used with the antibodies, growth factors and matrices of this invention.

The term "synthetic graft" means any artificial prosthesis having biocompatible characteristics. In one embodiment, the synthetic grafts can be made of polyethylene terephthalate (Dacron®, PET) or polytetrafluoroethylene (Teflon®, ePTFE). In another embodiment, synthetic grafts are comprised of for example, polyurethane, cross-linked PVA hydrogel, and/or biocompatible foams of hydrogels. In yet a third embodiment, a synthetic graft is composed of an inner layer of meshed polycarbonate urethane and an outer layer of meshed polyethylene terephthalate. It will be apparent to those skilled in the art that any biocompatible synthetic graft can be used with the matrices, pharmaceutical substance and ligands of this invention. (Bos et al. 1998. Small-Diameter Vascular Prostheses: Current Status. *Archives Physio Bio-*

*chem.* 106:100-115, incorporated herein by reference). Synthetic grafts can be used for end-to-end, end to side, side to end, side to side or intraluminal and in anastomosis of vessels or for bypass of a diseased vessel segments, for example, as abdominal aortic aneurysm devices.

In one embodiment, the matrix may further comprise naturally occurring substances such as collagen, fibronectin, vitronectin, elastin, laminin, heparin, fibrin, cellulose or carbon or synthetic materials. A primary requirement for the matrix is that it be sufficiently elastic and flexible to remain unruptured on the exposed surfaces of the stent or synthetic graft to the surrounding tissue.

In order to coat a medical device such as a stent, the stent may be dipped or sprayed with, for example, a liquid solution of the matrix of moderate viscosity. After each layer is applied, the stent is dried before application of the next layer. In one embodiment, a thin, paint-like matrix coating does not exceed an overall thickness of about 100 microns.

In one embodiment, the stent surface may be first functionalized, followed by the addition of a matrix layer. Thereafter, the antibodies are coupled to the surface of the matrix comprising the drug substance. In this aspect of the invention, the techniques of the stent surface creates chemical groups which are functional. The chemical groups such as amines, are then used to immobilize an intermediate layer of matrix, which serves as support for the ligands such as peptides and antibodies.

In another embodiment, a suitable matrix coating solution is prepared by dissolving 480 milligrams (mg) of a drug carrier, such as poly-D, L-lactid (available as R203 of Boehringer Inc., Ingelheim, Germany) in 3 milliliters (ml) of chloroform under aseptic conditions. In principle, however, any biodegradable (or non-biodegradable) matrix that is blood- and tissue-compatible (biocompatible) and can be dissolved, dispersed or emulsified may be used as the matrix if, after application, it undergoes relatively rapid drying to a self-adhesive lacquer- or paint-like coating on the medical device.

Barrier layers are applied to the coating by similar techniques as the layer of pharmaceutical substances and/or matrices are applied to the medical device, for example, by spraying, dipping or chemical evaporation techniques onto the medical device and where appropriate. In one embodiment, the barrier layer can be applied between layers of pharmaceutical composition. In another embodiment, the barrier layer can be applied on the outermost surface of the device and prior to applying the ligand layer. The barrier layer can also be applied in various thickness which can determine the delayed delivery of the pharmaceutical substance, for example, the thicker the layer is, the longer in time the delay would be in delivering the pharmaceutical substance. The thickness of the barrier layer can be determined depending on the patient's needs. In this embodiment, the pharmaceutical substance can be delivered at the site at an estimated time when required.

Application of Antibodies as Ligands to the Matrix—

Antibodies that promote adherence of progenitor endothelial cells are incorporated into the matrix, either covalently or noncovalently. Antibodies may be incorporated into the matrix layer by mixing the antibodies with the matrix coating solution and then applied the mixture to the surface of the device. In general, antibodies are attached to the surface of the outermost layer of matrix that is applied on the luminal surface of the device, so that the antibodies are projecting on the surface that is in contact with the circulating blood. For example, antibodies and other compounds such as peptides including growth factors can be applied to the surface matrix using standard techniques.

In one embodiment, the antibodies are added to a solution containing the matrix. For example, Fab fragments on anti-CD34 monoclonal antibody are incubated with a solution containing human fibrinogen at a concentration of between 500 and 800 mg/dl. It will be appreciated that the concentration of anti-CD34 Fab fragment will vary and that one of ordinary skill in the art could determine the optimal concentration without undue experimentation. The stent is added to the Fab/fibrin mixture and the fibrin activated by addition of concentrated thrombin (at a concentration of at least 1000 U/ml). The resulting polymerized fibrin mixture containing the Fab fragments incorporated directly into the matrix is pressed into a thin film (less than 100 μm) on the surface of the stent or synthetic graft. Virtually any type of antibody or antibody fragment can be incorporated in this manner into a matrix solution prior to coating of a stent or synthetic graft.

For example, in another embodiment, whole antibodies with or without antibody fragments can be covalently coupled to the matrix. In one embodiment, the antibodies and for example peptides such as growth factor(s) are tethered covalently the matrix through the use of hetero- or homobifunctional linker molecules. As used herein the term "tethered" refers to a covalent coupling of the antibody to the matrix by a linker molecule. The use of linker molecules in connection with the present invention typically involves covalently coupling the linker molecules to the matrix after it is adhered to the stent. After covalent coupling to the matrix, the linker molecules provide the matrix with a number of functionally active groups that can be used to covalently couple one or more types of antibody. FIG. 1A provides an illustration of coupling via a cross-linking molecule. An endothelial cell, 1.01, binds to an antibody, 1.03, by a cell surface antigen, 1.02. The antibody is tethered to the matrix, 1.05-1.06, by a cross-linking molecule, 1.04. The matrix, 1.05-1.06, adheres to the stent, 1.07. The linker molecules may be coupled to the matrix directly (i.e., through the carboxyl groups), or through well-known coupling chemistries, such as, esterification, amidation, and acylation. The linker molecule may be a di- or tri-amine functional compound that is coupled to the matrix through the direct formation of amide bonds, and provides amine-functional groups that are available for reaction with the antibodies. For example, the linker molecule could be a polyamine functional polymer such as polyethyleneimine (PEI), polyallylamine (PALLA) or polyethyleneglycol (PEG). A variety of PEG derivatives, e.g., mPEG-succinimidyl propionate or mPEG-N-hydroxysuccinimide, together with protocols for covalent coupling, are commercially available from Shearwater Corporation, Birmingham, Ala. (See also, Weiner et al., Influence of a poly-ethyleneglycol spacer on antigen capture by immobilized antibodies. *J. Biochem. Biophys. Methods* 45:211-219 (2000), incorporated herein by reference). It will be appreciated that the selection of the particular coupling agent may depend on the type of antibody used and that such selection may be made without undue experimentation. Mixtures of these polymers can also be used. These molecules contain a plurality of pendant amine-functional groups that can be used to surface-immobilize one or more antibodies.

Small molecules can comprise synthetic or naturally occurring molecules or peptides which can be used in place of antibodies or fragments thereof, or in combination with antibodies or antibody fragments. For example, lectin is a sugar-binding peptide of non-immune origin which occurs naturally. The endothelial cell specific Lectin antigen (*Ulex Europaeus* Uea 1) (Schatz et al. 2000 Human Endometrial Endothelial Cells Isolation, Characterization, and Inflammatory-Mediated Expression of Tissue Factor and Type 1 Plasminogen Activator Inhibitor. *Biol Reprod* 62: 691-697) can selectively bind the cell surface of progenitor endothelial cells.

Synthetic "small molecules" have been created to target various cell surface receptors. These molecules selectively bind a specific receptor(s) and can target specific cell types such as progenitor endothelial cells. Small molecules can be synthesized to recognize endothelial cell surface markers such as VEGF. For example, SU11248 (Sugen Inc.) (Mendel et al. 2003 In vivo antitumor activity of SU11248, a novel tyrosine kinase inhibitor targeting vascular endothelial growth factor and platelet-derived growth factor receptors: determination of a pharmacokinetic/pharmacodynamic relationship. *Clin Cancer Res*. January; 9(1):327-37), PTK787/ZK222584 (Drevs J. et al. 2003 Receptor tyrosine kinases: the main targets for new anticancer therapy. *Curr. Drug Targets*. February; 4(2):113-21) and SU6668 (Laird, A D et al. 2002 SU6668 inhibits Flk-1/KDR and PDGFRbeta in vivo, resulting in rapid apoptosis of tumor vasculature and tumor regression in mice. FASEB J. May; 16(7):681-90) are small molecules which bind to VEGFR-2.

In another embodiment, another subset of synthetic small molecules which target the endothelial cell surface are, for example, the alpha(v) beta(3) integrin inhibitors, SM256 and SD983 (Kerr J S. et al. 1999 Novel small molecule alpha v integrin antagonists: comparative anti-cancer efficacy with known angiogenesis inhibitors can be used. Anticancer Res March-April; 19(2A):959-68). SM256 and SD983 are both synthetic molecules which target and bind to alpha(v) beta (3) present on the surface of endothelial cells.

The invention also relates to a method of treating a patient having vascular disease, such as artherosclerosis, and in need of such treatment with the coated medical device of the invention. The method comprises implanting into a patient in need of the treatment a coated medical device of the invention. In the embodiment where the endothelial cells are genetically-altered, the cells can be provided to the patient at the site of implantation of the coated device by infusion, or administering the cells into the blood stream after implantation of the device. The methods of the invention may be practiced in vivo or in vitro.

Figure 1B:
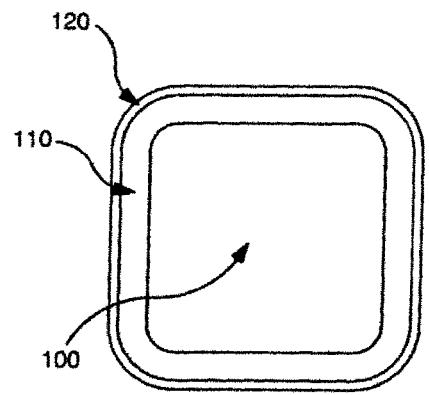
FIG. 1B is a cross section of the stent strut in FIG. 1A.
Figure 2A:
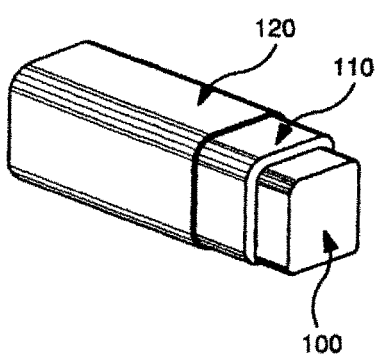
FIG. 2A and FIG. 2B (cross-section) are schematic representations of an embodiment in which a stent strut comprises a ligand (outer) layer and a drug/polymer layer surrounding about three quarters of the circumference of the strut.
Figure 2B:
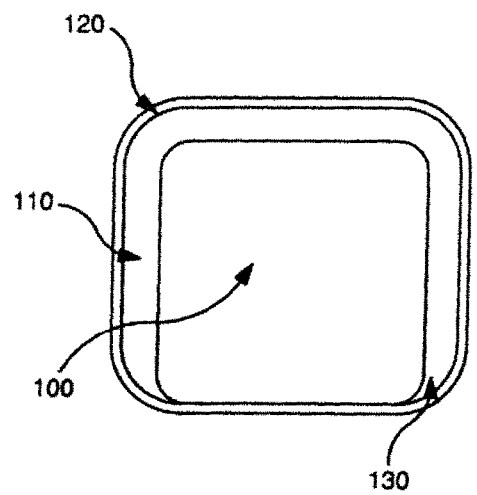

The coating of the invention can be applied using various techniques available in the art, such as dipping, spraying, vapor deposition, injection like and/or dot matrix-like approach. For example, FIGS. 1A and 1B illustrate a simple pattern of cell capturing and drug delivery mechanism in which a stent strut 100 is shown with a continuous coating of a drug/polymer matrix layer 110 applied to the strut surface and a ligand layer 120 on top of the drug/polymer composition. FIGS. 2A and 2B illustrate an alternate embodiment of the invention in which the drug/polymer layer 110 is a discontinuous layer 130, however, the amount of drug/polymer matrix composition greater than the, for example, that shown in FIGS. 2A and 2B.

Figure 3A:
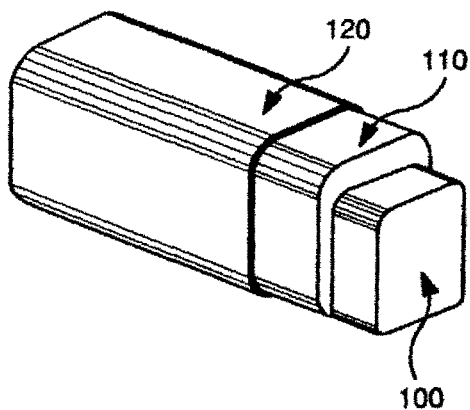
FIGS. 3A and 3B (cross-section) are schematic representations of an embodiment in which a stent strut comprises a ligand (outer) layer and a drug/polymer layer surrounds three quarters of the circumference of the strut and drug/polymer concentration is greater in the middle section of the layer surrounding the strut.
Figure 3B:
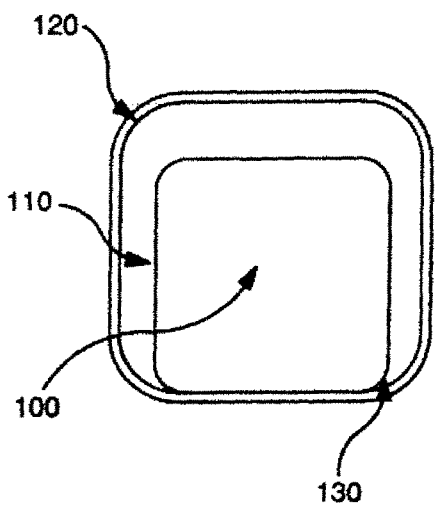

FIGS. 3A and 3B show an alternate embodiment in which the drug/polymer layer is discontinuous. In this embodiment, the drug/polymer composition is applied to about ¾ of the circumference of the device, however, the middle one third 140 of the layer 110 comprises the greatest amount of the drug composition, and the ligand layer is applied on top of drug/polymer layer. FIGS. 4A, 4 B and 4C show yet another embodiment with respect to the application of the coating. In this embodiment of the invention, the drug/polymer matrix composition is applied to a portion of the surface of the medical device 100 in a dot matrix like pattern 150. As seen in FIGS. 4A-C, the ligand layer 120 is applied to surrounds the entire circumference of the medical device including the drug/polymer composition 110.

In yet another embodiment, FIGS. 5A and 5B show a medical device 100 coated with a drug/polymer matrix composition which is concentrated in a small section of the surface 110 of the device 100. In this aspect of the invention, the ligand layer 120 covers the entire circumference of the device including the drug/polymer composition 110. FIGS. 6A-6C show an alternate embodiment in which the ligand layer 120 is applied to cover the surface of device 100 and in a section of the surface of ligand layer 120, a drug/polymer matrix composition 150 is applied on the device. FIGS. 7A, 7B and 7C show an alternate embodiment, in which the device can be covered with multiple layers of drug/polymer matrix composition 110, 150 applied as a continuous layer 110 on the surface of the device 100, followed by a ligand layer 120 and an additional drug/polymer matrix discontinuous layer in a dot matrix like patter 150 on the surface of the ligand layer 120.

Additional alternate embodiments are shown in FIGS. 8A and 8B. In this aspect of the invention, the medical device, in this case a stent strut is coated with a ligand layer 120 and a drug/polymer matrix layer in a dot matrix pattern 150 can be partially applied on device on top of the ligand layer (FIG. 8A) or below (FIG. 8B) the ligand layer.

FIGS. 9A-9C and 10A-10B show other embodiments of the invention in cross-section. As seen in FIGS. 9A-9C, the ligand, such as an antibody is shown as the outermost layer on the surface of the coated medical device, and the coating can comprise additional intermediate layers, which comprise the drug/polymer composition and optionally additional components. FIGS. 10A-1, 10A-2 and 10A-3 additionally illustrate a basement membrane and an intermediate layer coating the device.

Figure 10B:
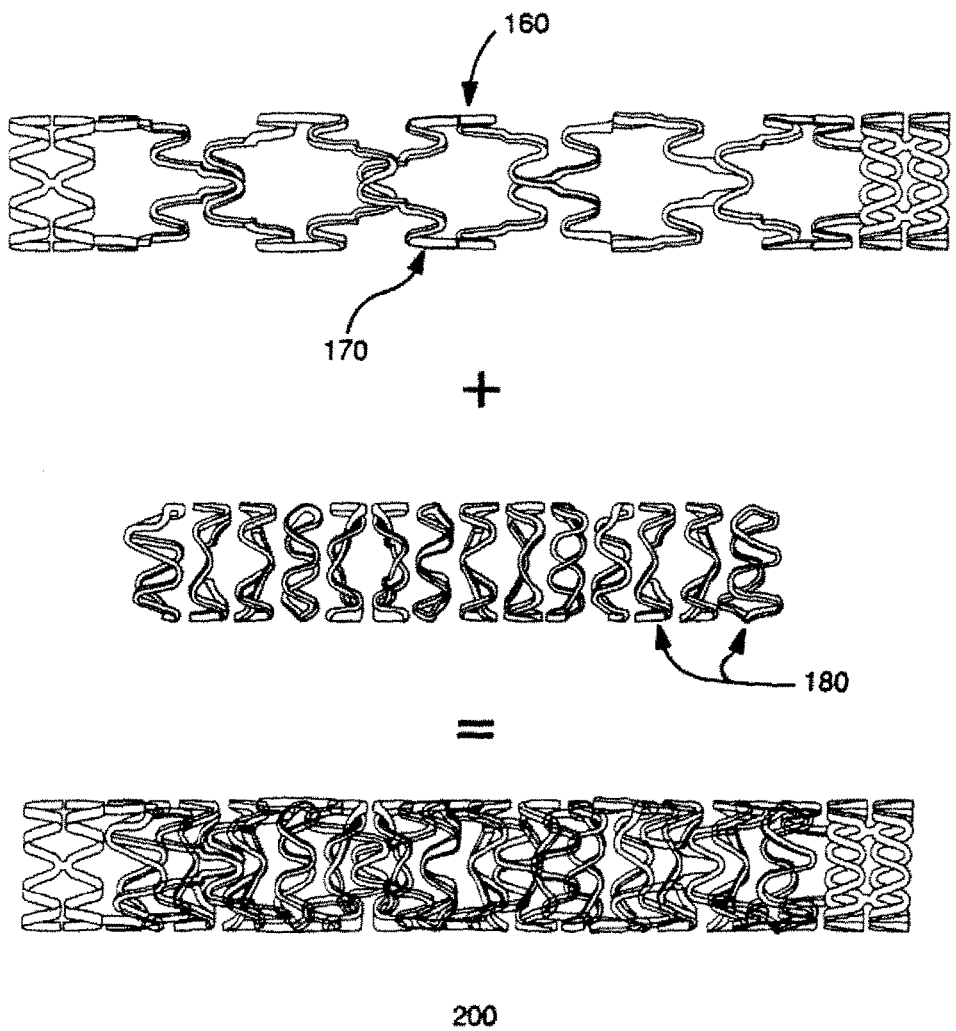
FIG. 10B is a schematic representation of an embodiment in which a stent's component parts, i.e., helices, rings and ends are coated with different coating components.

In another embodiment comprising a stent, the coating composition comprising a drug/polymer matrix, can be applied to portions of the stent such as the spine or helical element of a stent. In this aspect of the invention, the remaining surfaces of the stent not covered with the drug/polymer matrix can be coated with the ligand layer on portions of the stent surface or the entire remaining surface of the stent as illustrated in FIG. 10B. In the embodiment in FIG. 10B, the pharmaceutical release component and the antibody modified surface are exposed on alternating surfaces of the device. This allows for more targeted treatment of segments of the vessel (such as the healthier tissue at the leading and trailing ends of the stent versus the highly diseased middle portion of the stent, i.e., center of the lesion) and minimizes the interaction between the pharmaceutical component the antibody surface, and the newly adhered endothelial cells on the surface of the stent.

As illustrated in FIG. 10B, the stent ends component may be comprised of for example, an antibody or a small molecule (EPC capture) surface. Helix component 160 can comprised of a basement membrane base coating, and helix segment 170 represents a slow release pharmaceutical component that can be comprised of a non-degradable biocompatible polymer matrix that elutes an agent for maintaining long term vessel patency such as eNOS, tPA, statins, and/or antibiotics. FIG. 10B also shows the ring component 180 of the stent can be comprised of a fast release pharmaceutical agent to retard early neointimal hyperplasia/smooth muscle cell migration, and the entire stent 200 is therefore coated with different coating in each portion of the device.

The following examples illustrate the invention, but in no way limit the scope of the invention.

Example 1

Preparation of Coating Composition

Figure 12:
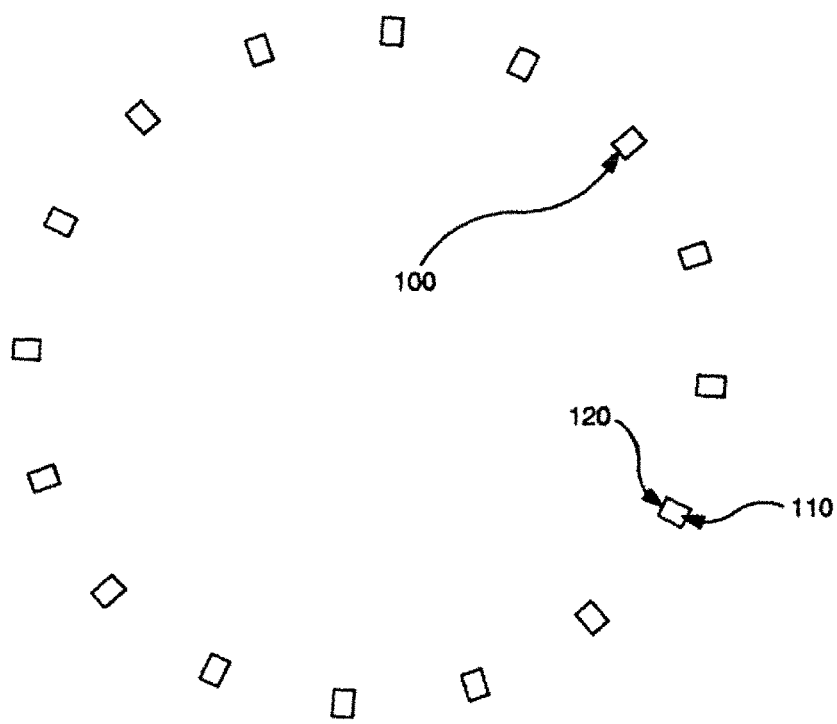
FIG. 12 is a schematic representation of a cross-section of a stent showing the layers of the coating.

The polymer Poly DL Lactide-co-Glycolide (DLPLG, Birmingham Polymers) is provided as a pellet. To prepare the polymer matrix composition for coating a stent, the pellets are weighed and dissolved in a ketone or methylene chloride solvent to form a solution. The drug is dissolved in the same solvent and added to the polymer solution to the required concentration, thus forming a homogeneous coating solution. To improve the malleability and change the release kinetics of the coating matrix, the ratio of lactide to glycolide can be varied. This solution is then used to coat the stent to form a uniform coating as shown in FIG. 11. FIG. 12 shows a cross-section through a coated stent of the invention. The polymer(s)/drug(s) composition can be deposited on the surface of the stent using various standard methods.

Example 2

Evaluation of Polymer/Drugs and Concentrations

Process for Spray-Coating Stents: The polymer pellets of DLPLG which have been dissolved in a solvent are mixed with one or more drugs. Alternatively, one or more polymers can be dissolved with a solvent and one or more drugs can be added and mixed. The resultant mixture is applied to the stent uniformly using standard methods. After coating and drying, the stents are evaluated. The following list illustrates various examples of coating combinations, which were studied using various drugs and comprising DLPLG and/or combinations thereof. In addition, the formulation can consist of a base coat of DLPLG and a top coat of DLPLG or another polymer such as DLPLA or EVAC 25. The abbreviations of the drugs and polymers used in the coatings are as follows: MPA is mycophenolic acid, RA is retinoic acid; CSA is cyclosporine A; LOV is Lovastatin™ (mevinolin); PCT is Paclitaxel; PBMA is Poly butyl methacrylate, EVAC is ethylene vinyl acetate copolymer; DLPLA is Poly (DL Lactide), DLPLG is Poly(DL Lactide-co-Glycolide).

Examples of the coating components and amounts (%) which can be used in the invention comprise:
1. 50% MPA/50% Poly L Lactide
2. 50% MPA/50% Poly DL Lactide
3. 50% MPA/50% (86:14 Poly DL Lactide-co-Caprolactone)
4. 50% MPA/50% (85:15 Poly DL Lactide-co-Glycolide)
5. 16% PCT/84% Poly DL Lactide
6. 8% PCT/92% Poly DL Lactide
7. 4% PCT/92% Poly DL Lactide
8. 2% PCT/92% Poly DL Lactide
9. 8% PCT/92% of (80:20 Poly DL Lactide/EVAC 40)
10. 8% PCT/92% of (80:20 Poly DL Lactide/EVAC 25)
11. 4% PCT/96% of (50:50 Poly DL Lactide/EVAC 25)
12. 8% PCT/92% of (85:15 Poly DL Lactide-co-Glycolide)
13. 4% PCT/96% of (50:50 Poly DL Lactide-co-Glycolide)
14. 25% LOV/25% MPA/50% of (EVAC 40/PBMA)
15. 50% MPA/50% of (EVAC 40/PBMA)
16. 8% PCT/92% of (EVAC 40/PBMA)
17. 8% PCT/92% of EVAC 40
18. 8% PCT/92% EVAC 12
19. 16% PCT/84% PBMA
20. 50% CSA/50% PBMA
21. 32% CSA/68% PBMA
22. 16% CSA/84% PBMA

Example 3

Figure 13:
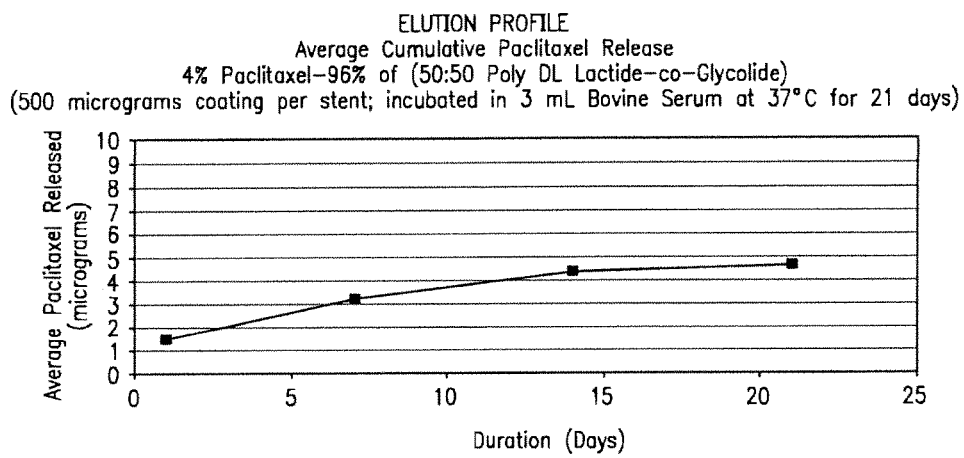
FIG. 13 is a graph showing the elution profile of a drug-coated stent, incubated for 21 days in bovine serum albumin, wherein the coating comprised 500 µg of 4% Paclitaxel and 96% polymer. The polymer used in the coating was 50:50 Poly(DL Lactide-co-Glycolide).

The following experiments were conducted to measure the drug elution profile of the coating on stents coated by the method described in Example 2. The coating on the stent consisted of 4% Paclitaxel and 96% of a 50:50 Poly(DL-Lactide-co-Glycolide) polymer. Each stent was coated with 500 .mu.g of coating composition and incubated in 3 ml of bovine serum at 37.degree. C. for 21 days. Paclitaxel released into the serum was measured using standard techniques at various days during the incubation period. The results of the experiments are shown in FIG. 13. As shown in FIG. 13, the elution profile of Paclitaxel release is very slow and controlled since only about 4 μg of Paclitaxel are released from the stent in the 21-day period.

Example 4

Figure 14:
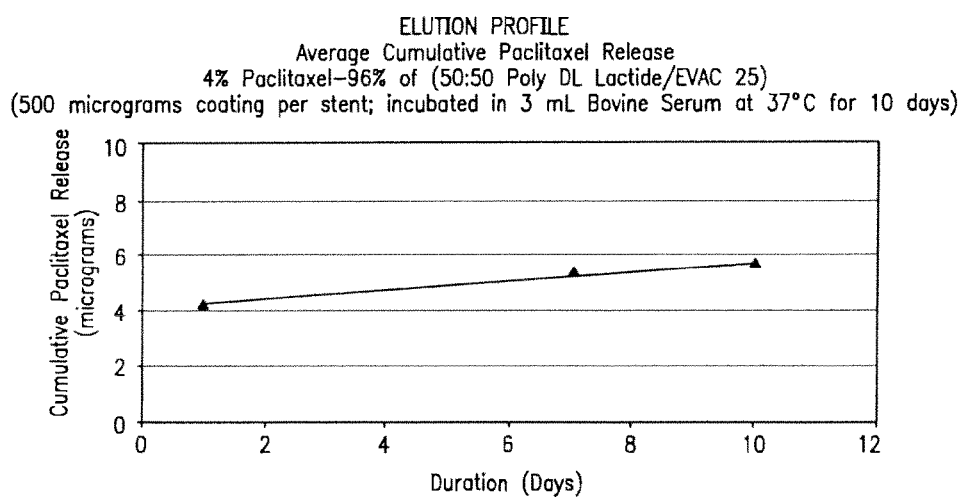
FIG. 14 is a graph showing the elution profile of a drug-coated stent, incubated for 10 days in bovine serum albumin, wherein the coating comprised 500 µg of 8% Paclitaxel and 92% polymer. The polymer used in the coating was 50:50 Poly(DL Lactide-co-Glycolide)/EVAC 25.

The following experiments were conducted to measure the drug elution profile of the coating on stents coated by the method describe in Example 2. The coating on the stent consisted of 4% Paclitaxel and 92% of a 50:50 of Poly(DL-Lactide) and EVAC 25 polymer. Each stent was coated with 500 μg of coating composition and incubated in 3 ml of bovine serum at 37° C. for 10 days. Paclitaxel released into the serum was measured using standard techniques at various days during the incubation period. The results of the experiments are shown in FIG. 14. As shown in FIG. 14, the elution profile of Paclitaxel release is very slow and controlled since only about 6 μg of Paclitaxel are released from the stent in the 10-day period.

Example 5

Figure 15:
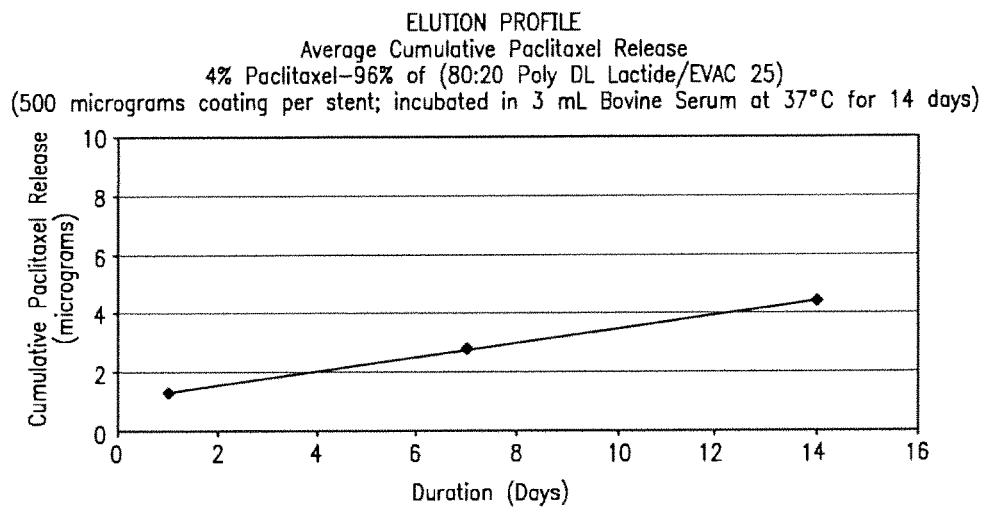
FIG. 15 is a graph showing the drug elution profile of a drug-coated stent incubated for 10 days in bovine serum, wherein the coating comprised 500 µg of 8% Paclitaxel and 92% polymer. The polymer used in the coating was 80:20 Poly-DL Lactide/EVAC 25.

The following experiments were conducted to measure the drug elution profile of the coating on stents coated by the method describe in Example 2. The coating on the stent consisted of 8% Paclitaxel and 92% of a 80:20 of Poly(DL-Lactide) and EVAC 25 polymer. Each stent was coated with 500 μg of coating composition and incubated in 3 ml of bovine serum at 37° C. for 14 days. Paclitaxel released into the serum was measured using standard techniques at various days during the incubation period. The results of the experiments are shown in FIG. 15. As shown in FIG. 15, the elution profile of Paclitaxel release is very slow and controlled since only about 4 μg of Paclitaxel are released from the stent in the 14-day period.

Example 6

Figure 16:
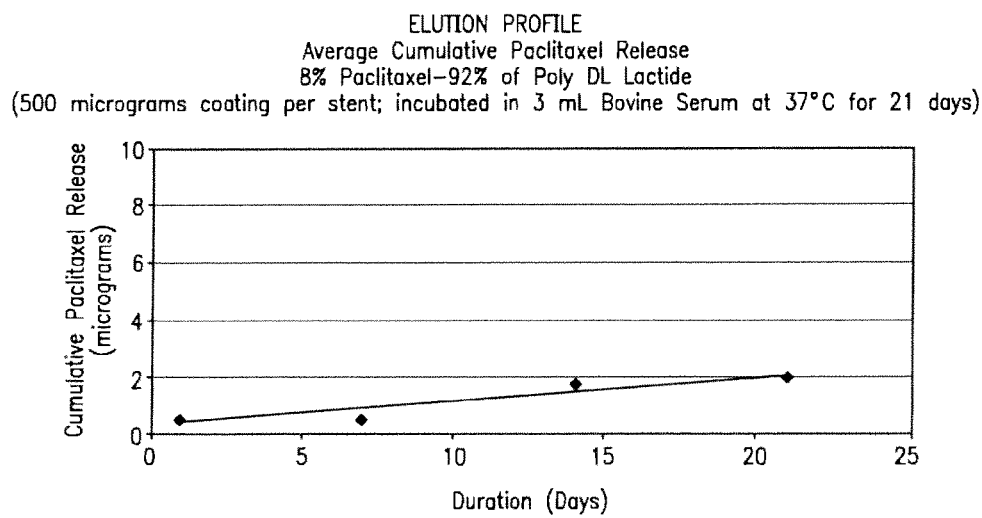
FIG. 16 is a graph showing the drug elution profile of a drug-coated stent, incubated for 21 days in bovine serum albumin, wherein the coating comprised 500 µg of 8% Paclitaxel and 92% poly(DL-Lactide) polymer.

The following experiments were conducted to measure the drug elution profile of the coating on stents coated by the method describe in Example 2. The coating on the stent consisted of 8% Paclitaxel and 92% of Poly(DL-Lactide) polymer. Each stent was coated with 500 μg of coating composition and incubated in 3 ml of bovine serum at 37° C. for 21 days. Paclitaxel released into the serum was measured using standard techniques at various days during the incubation period. The results of the experiments are shown in FIG. 16. As shown in FIG. 16, the elution profile of Paclitaxel release is very slow and controlled since only about 2 μg of Paclitaxel are released from the stent in the 21-day period. The above data show that by varying the polymer components of the coating, the release of a drug can be controlled for a period of time required.

Example 7

In this experiments, the elution profile of stents coated with a composition comprising 92% PGLA and 9% paclitaxel as described in Example 2 were measured. Elution testing is used to provide data for the release kinetics of the paclitaxel from the polymer matrix. The release of the paclitaxel into bovine calf serum at 37° C. was used to approximate the in vivo conditions. While serum is similar to blood, this simulation does not necessarily reflect the actual release kinetics of the implanted device. This simulation provides a repeatable, controlled environment from which relative release may be evaluated. Elution data is collected on sets of paclitaxel coated stents comprised of 0.13, 0.20, 0.29, 0.38 μg/mm² paclitaxel. The 0.13 and 0.26 ug/mm² units were evaluated in animal testing studies.

Figure 17:
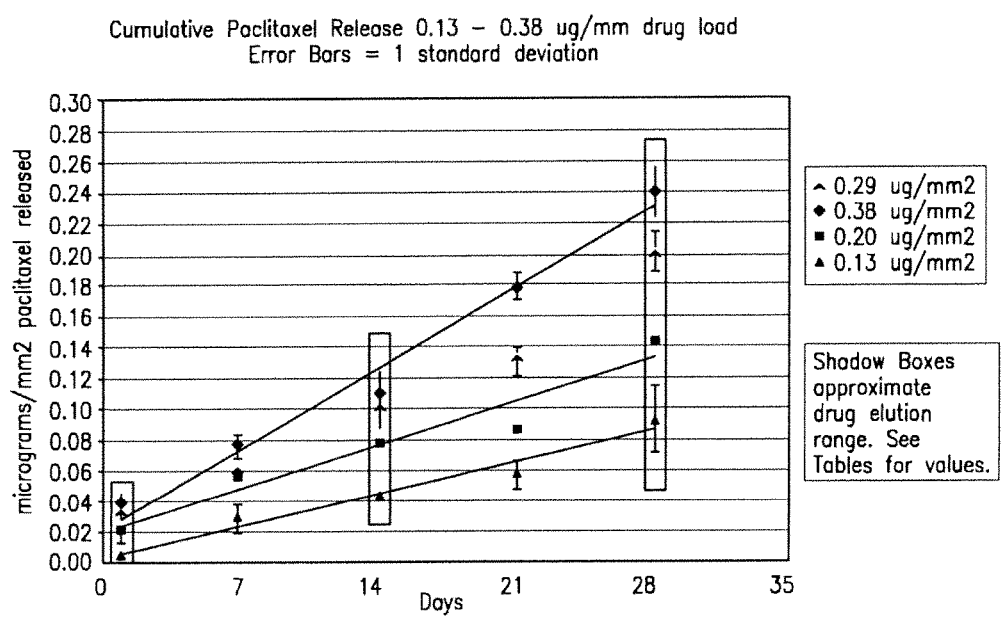
FIG. 17 is a graph showing the elution profile of drug-coated stent incubated for 1, 14, and 28 days in serum albumin, wherein the coating comprised Paclitaxel and PGLA.

Elution Test Method:

Coated stents are placed in bovine calf serum at 37° C. At designated time points, the stents are removed from the serum. The residual paclitaxel is extracted from the coating. The amount of paclitaxel released is calculated by subtracting the amount of paclitaxel remaining on the stent from the original loaded amount of paclitaxel loaded onto the stent. FIG. 17 demonstrates the amount of paclitaxel released per square millimeter of stent surface. Table 1 shows the range of in vitro release kinetics at 1, 14 and 28 days. As seen in FIG. 16 and Table 1, the release kinetics of the coating is slow as the paclitaxel ranges from 0 to 0.051 μg/mm² on Day 1 to 0.046 to 0.272 μg/mm² on Day 28.

TABLE 1

|  | 1 Day Micrograms/mm² | 14 Days Micrograms/mm² | 28 Days Micrograms/mm² |
|---|---|---|---|
| Average | 0.021 | 0.087 | 0.158 |
| Maximum | 0.051 | 0.148 | 0.272 |
| Minimum | 0.00 | 0.023 | 0.046 |

Example 8

Additional serum elution data were performed out to 70 days and 48 days with stents coated with 4% Paclitaxel/96% PGLA and 100% PGLA respectively. The elution of paclitaxel is monitored by analyzing the amount of paclitaxel in the serum out to 42 days as reported. A test method which monitors the amount of residual paclitaxel on the stent is used to characterize the elution at 90 days for TG0331A. The residual paclitaxel on 5 stents available for testing gave an average of 2.29 micrograms (range 1.87-2.86) maximum.

Figure 18:
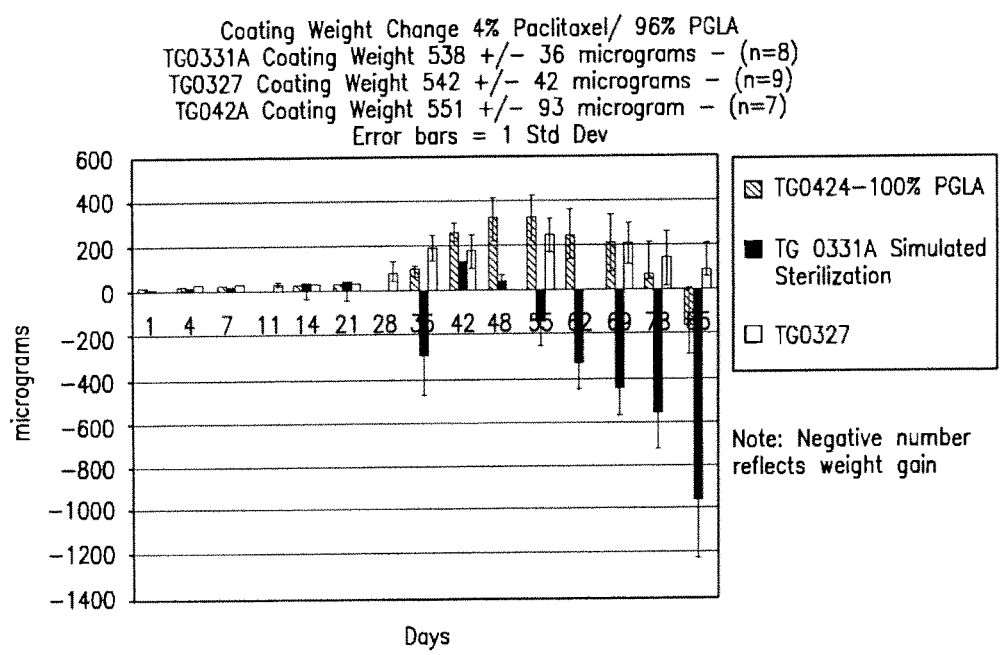
FIG. 18 is a graph showing drug elution test results of a stent coated with 4% Paclitaxel in 96% PGLA polymer matrix and in 100% PGLA incubated in serum albumin for up to 70 days.
Figure 19A:
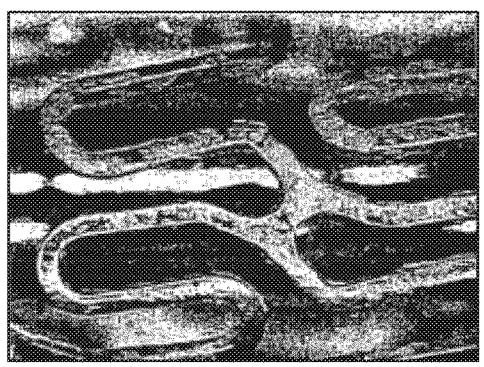
FIGS. 19A-19D are photographs of drug-coated stents after 90 days (FIGS. 19A and 19B) and 84 days (FIGS. 19C and 19D) after incubation on serum albumin.
Figure 19B:
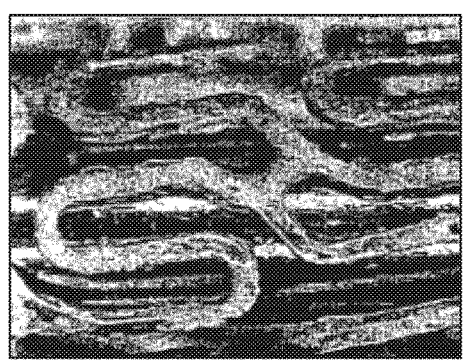
Figure 19C:
Figure 19D:
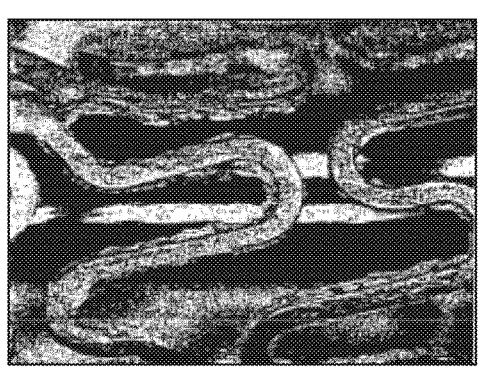

The weight of the coated stents was measured at specified time points during the elution in serum at 37° C. Comparison of non-treated and simulated sterilization units (40° C., 18 hours) demonstrates a difference in the weight loss profile. Also the weight loss of PGLA without drug is shown for comparison. FIG. 18 shows the results of these experiments. As seen in FIG. 18, simulated sterilization causes a gain in weight of the coated stents.

At each time point during the experiments, the stent coatings are microscopically examined and photographs. Table 2 below shows some visual characteristics of the Samples #1-3.

TABLE 2

| Sample No. | Description | Time points | Observation * |
|---|---|---|---|
| 1 | 4% Paclitaxel Simulated Sterilization | 63 Days | Coating no longer has smooth appearance and some areas where no coating present |
|  |  | 70 Days | Similar to 63 days, with more coating missing, but not as much missing as 78 days for TG0327 |
|  |  | 84 Days | Similar to sample #3 at 48 and 62 days |
| 2 | 4% Paclitaxel (no sim sterile) | 21 Days | Smooth coating, white appearance, some bubbles on surface |
|  |  | 28 Days | Coating no longer smooth, some coating missing |
|  |  | 78 Days | Similar to TG0331A with more coating missing |
|  |  | 90 Days | Similar to sample #3 at 62 Days. |
| 3 | 100% PGLA | 48 Days | Coating not smooth and some coating missing |
|  |  | 62 Days | Significant areas of stent with coating missing. |
|  |  | 90 Days | Small amounts of remaining coating. |

FIG. 19A-19D shows that virtually all the drug present in the coating has eluted after 90 days of serum incubation, while some polymer matrix remains attached to the stent. The combination of weight change, drug elution, and microscopic evaluation provides a good characterization of the coated surface. Both Samples #2 and #3 did not see the simulated sterilization condition and responded more similarly. The samples subjected to simulated sterilization conditions, Sample #1 appears to have a slower degradation rate of the coating in serum. A trend is seen in the coating appearance under microscope that the amount of coating remaining for this group. This makes sense as the simulated sterilization conditions is just below the Tg of the polymer and may cause some annealing of the material.

The drug elution at 90 days demonstrates that virtually all the drug has been eluted from the coating. The amount of drug measured is a maximum as degraded polymer will also result in some absorbance at the test wavelength. Considering testing on other lots for residual drug demonstrated roughly 80% of the drug is eluted after 28 days in serum.

These results provide evidence that the polymer is still present but that the drug is substantially eluted at 90 days from a 4% paclitaxel loaded PGLA matrix in serum.

Example 9

Endothelial Cell Capture by anti-CD34 coated Stainless Steel Disks: Human Umbilical Vein Endothelial Cells (HU-VEC) (American Type Culture Collection) are grown in endothelial cell growth medium for the duration of the experiments. Cells are incubated with dextran and gelatin coated samples with or without bound antibody on their surface or bare stainless steel (SST) samples. After incubation, the growth medium is removed and the samples are washed twice in PBS. Cells are fixed in 2% paraformaldehyde (PFA) for 10 minutes and washed three times, 10 minutes each wash, in PBS, to ensure all the fixing agent is removed. Each sample is incubated with blocking solution for 30 minutes at room temperature, to block all non-specific binding. The samples are washed once with PBS and the exposed to 1:100 dilution of VEGFR-2 antibody and incubated overnight. The samples are subsequently washed three times with PBS to ensure all primary antibody has been removed. FITC-conjugated secondary antibody in blocking solution is added to each respective sample at a dilution of 1:100 and incubated for 45 minutes at room temperature on a Belly Dancer apparatus. After incubation, the samples are washed three times in PBS, once with PBS containing 0.1% Tween 20, and then again in PBS. The samples are mounted with Propidium Iodine (PI) and visualized under confocal microscopy.

FIGS. 20A-4E are photomicrographs of SST samples coated with dextran and anti-CD34 antibody (FIG. 20A), gelatin and anti-CD34 antibody coated (FIG. 20B), bare SST (FIG. 20C), dextran coated and no antibody (FIG. 20D) and gelatin-coated and no antibody (FIG. 20E). The figures show that only the antibody coated samples contain numerous cells attached to the surface of the sample as shown by PI staining. The bare SST control disk shows few cells attached to its surface.

FIGS. 21A-21C are photomicrographs of control samples dextran-coated without antibody bound to its surface. FIG. 21A shows very few cells as seen by PI staining adhered to the surface of the sample. FIG. 21B shows that the adherent cells are VEGFR-2 positive indicating that they are endothelial cells and FIG. 21C shows a combination of the stained nuclei and the VEGFR-2 positive green fluorescence. FIGS. 21D-F are photomicrographs of control samples coated with gelatin without antibody on its surface. FIG. 21D shows no cells are present since PI staining is not present in the sample and there is no green fluorescence emitted by the samples (see FIGS. 21E and 21F).

FIGS. 22A-22C are photomicrographs of dextran coated SST samples having anti-CD34 antibody bound on its surface. The figures show that the samples contain numerous adherent cells which have established a near confluent monolayer (FIG. 22A) and which are VEGFR-2 positive (FIGS. 22B and 22C) as shown by the green fluorescence. Similarly, FIGS. 22D-22F are photomicrographs of a gelatin-coated sample with anti-CD34 antibody bound to its surface. These figures also show that HUVECs attached to the surface of the sample as shown by the numerous red-stained nuclei and green fluorescence from the VEGFR-2/FITC antibody (FIGS. 22E and 22F).

Example 10

Transfection of porcine Endothelial Progenitor Cells (EPCs) with a Bicistronic Vector Encoding Both a Vasodilatory Compound and a Unique Cell Surface Marker (truncated MHC-I). MHC-I can be recognized by a specific antibody immobilized on an intravascular prosthesis. Antibody coated stents are implanted into the coronary arteries of pigs, followed by transplantation of the genetically modified EPCs into the pigs. EPCs are captured by the coated stent due to the antibody-antigen interaction and an endothelial monolayer formed over the stent struts. The captured cells can secrete the over-expressed vasodilator, increasing distal flow, and trigger positive remodeling.

Plasmid selection: The MACSelect K System consisting of the pMASCSK$^k$ plasmid vector has been developed by Miltenyi Biotec (Germany). The pMACSK .II plasmid is a bicistronic vector (5229 bp) containing a multiple cloning site (MCS) in which a cDNA encoding the prostacyclin synthase gene is cloned, as well as the gene encoding a truncated mouse MHC class I molecule, H-2K. This system was developed to select for transfected cells, with the truncated MHC molecule acting as the selection marker. Native H-2K expression is restricted to some rare murine strains (eg. AKRiJA or CBNJ), therefore, a monoclonal antibody to the H-2K$^k$ surface protein (Miltenyi Biotec) should be substantially free of extraneous reactivity with other surface antigens.

Assessment of cross-reactivity with whole blood: In order to ensure that the anti-H-2K$^k$ antibody does not crossreact with cellular components of whole porcine blood, whole blood is reacted with FITC-conjugated anti-H-2K antibody and subjected to whole blood FACS analysis (Beckman Coulter Cytomics FC 500). As a positive control whole blood is "spiked" with the mouse spleen fibroblast cell line AKRIJASp (American Type Culture Collection (ATCC)), which expresses the H-2K$^k$ surface antigen.

Fibroblast culture: AKR/JA.Sp fibroblast cells are cultured in non-coated T-75 plastic flasks (Sarstedt, Montreal) using Dulbeccos's Modified Eagle's Medium (DMEM) formulated with 4 mM L-glutamine, 4500 mg/L glucose, 1 mM sodium pyruvate, 1500 mg/L sodium bicarbonate, and 10% Fetal Bovine Serum at 37° C. and 5% $CO_2$. Cells dissociation is performed using trypsin/EDTA (Invitrogen). H-2K$^k$ expression is confirmed by immunohistochemical analysis using fluorescence labeled H-2K$^k$ antibody. Briefly, cells are plated at $0.5 \times 10^6$ cells/cm$^2$ in 2-well non-coated chamber slides. Cultures are fixed at days 1, 2, 3, and 4 with 2% paraformaldehyde and stained with FITC-conjugated H-2K antibody (Miltenyi Biotec, Germany) and the nuclear marker propidium iodide (PI) (Vectashield Mounting Medium, Vector Laboratories). Analysis and quantification are performed using confocal microscopy (Nikon Eclipse E800 Biorad Radiance 2 100). Human fibroblasts are used as a negative control.

Analysis of non-adherent cells: AKRIJA.Sp cells in a non-adherent form are characterized for the retention of H-2K$^k$ surface protein in order to confirm the feasibility of using this system in the presence of blood. Cells are cultured as described above in T-75, non-coated flasks. Adherent cells at day 4 are disassociated using Trypsin/EDTA and the number of cells expressing H-2K$^k$ surface proteins is determined using FITC-conjugated H-2K$^k$ antibody and FACS analysis (Beckman Coulter Cytomics FC500). FITC-labeled mouse IGg2a isotype is used as a negative control.

Plasmid construction: cDNA encoding prostacyclin synthase is cloned into the bicistronic plasmid vector pMACS K$^{kO}$.II (Miltenyi Biotec, Germany) using BamHI and HindIII restriction sequences at the multiple cloning site. A cDNA of 1153 base pairs containing a prostacyclin synthase gene and pVAX-1 in a plasmid construct is used. Transformation of HG70 *E coli* is performed in the presence of ampicillin (50 ng/ml) as a selection agent.

Complete cDNA for human α-CGRP was obtained from Open Biosystems (Catalog #MHS 1768-9 1441 17; Huntsville Ala.) in the plasmid vector pPCR-Script Amp SK(+). The fragment is then ligated with BamHI/EcoRI into the bicistronic plasmid vector pMACS K .II. JM109 *E coli* is transformed to obtain large amounts of the plasmid.

EPC transfection: Porcine mononuclear cells are enriched from whole blood from pigs by Ficoll density centrifugation, and EPCs isolated by enriched culture as described above. After day 7 in culture the EPCs are transfected with the bicistronic plasmid vector containing the transgene containing the α-CGRP or prostacyclin synthase using nucleoporation (Amaxa Nucleofector, Germany), Electroporation transfection efficiencies of >70% of EPCs have been obtained using both a reporter gene and endothelial nitric oxide synthase (eNOS) in the pVAXt plasmid (data not shown). EPCs which have been successfully transfected and expressing H-2K$^k$ surface proteins are purified and isolated using MACS Dead cell removal kit, MACSelect $K^k$ Micro-Beads and MS Separation Column (Miltenyi Biotec). MACSelect $K^k$ MicroBeads are biodegradable, and are lost with cell culture within 24 hours.

Measurement of vasodilator expression: Measurement of prostacyclin synthase activity: Transfected EPCs are maintained in culture after transfection for 2 days. The medium is changed, and prostacyclin synthase activity is assessed by measuring the level of the metabolite of prostacyclin synthase, 6-ketoprostaglandin Fla (6-keto-PGFlcu) in the medium by radioimmunoassay (Amersham Corp.) per the manufacturer's instructions.

Measurement of α-CGRP activity: α-CGRP expression is determined in transfected cells using the Immunohistochemistry Staining Kit (Bachem USA). Transfected EPCs in culture for 3 days are fixed in methanol at −10° C. for 5 minutes. The cells are washed and allowed to air dry. To quench endogenous peroxide activity the fixed cells are incubated in 0.5% solution of hydrogen peroxide in PBS for 7 minutes. To block nonspecific binding, the cells are incubated in serum block for 20 minutes. Cells are then treated with the primary antibody anti-α-CGRP (rabbit monoclonal, Bachem) at three dilutions, 1:100, 1:200 and 1:500 for 2 h. The slides are then washed and exposed to biotinylated secondary antibody for 30 minutes. The cells are then rinsed and treated for 30 minutes with HRP-strepavidin complex. After a PBS wash, the cells are exposed to a substrate-chromogen mixture for 3 minutes. The reaction is stopped by the addition of deionized water. The slides are counterstained with Mayer's hematoxylin for 3 minutes. The slides are then washed in tap water, placed in PBS until they turned blue, then rinsed with distilled water. The slides are then dehydrated using 95% and 100% ethanol and xylene. The slides are coverslipped and examined under light microscopy.

Antibody coated stents: Stainless steel stents (9 mm long) are coated with dextran and anti-H-$2K^k$ antibody as previously described.

In vivo cell capture: All experiments are performed in male Juvenile Yorkshire swine (>30 kg). Arterial access is obtained through an arteriotomy performed in the left carotid artery. After the administration of 200 μg of intracoronary nitroglycerin, coronary angiograms are obtained, and on-line quantitative coronary angiographic assessment performed. Stents are deployed 1.1:1 stent to vessel randomly to proximal segments of either the LAD, circumflex or right coronary arteries. Once implanted, 200 μg of intracoronary nitroglycerin is administered. Intravascular ultrasound (IVUS) is then performed to determine vessel caliber using a distal side-branch and the distal margin of the deployed stent as distal and proximal references. Administration of cells transfected with the bicistronic vector encoding either prostacyclin synthase or a-CGRP cells are accomplished using a prototype tandem balloon catheter (Cordis Corporation). The catheter consists of two highly compliant balloons located near the distal end of the device that are inflated through a single inflation port. Once inflated, a region of the vessel 1.0 cm in length is isolated between the balloons creating a localized infusion chamber. Distal blood flow is provided by a central lumen, and solutions are infused or aspirated throughout the chamber via two separated lumens. The infusion lumen terminates near the distal balloon, and the evacuation lumen terminates with one port near the proximal balloon. The tandem balloon catheter is advanced to the site of stent implantation and the balloons inflated to 25 psi (1.7 atm). Saline is delivered through the instillation port until the isolated segment is free of blood. Stented arterial segments are randomized to receive either a saline infusion or cell delivery. A total of $3 \times 10^6$ EPCs are given in 2 mls of cell suspension an infusion rate of 200 μL/min over 10 minutes, followed by 10 minutes incubation time. The arteriotomy site is then closed, and the animals allowed to recover. Animals are housed for 28 days after the cell treatment. A total of 34 animals are treated (10 saline control, 14 prostacyclin synthase, 14 α-CGRP). Two animals from each group are sacrificed one hour after cell delivery. The stented segments are explanted and flushed stented arterial segments are prepared for SEM by fixation in 10% buffered formalin PBS for 30 seconds and further fixed in 2% PFA with 2.5% glutaraldehyde (BDH Inc.) in 0.1 M sodium cacodylate buffer (Sigma) overnight. Post-fixation is completed with 1% osmium tetroxide (Sigma) in 0.1M cacodylate buffer followed by serial dehydration with ethanol and subsequent critical point drying with $CO_2$. After drying, samples are gold sputtered and visualized under scanning electron microscopy (SEM) for the presence of cells bound to the stent struts. Two animals from the prostacyclin synthase group and 2 animals from the α-CGRP group are sacrificed 5 days after stent implantation. The explanted stented arterial segments are placed in a 10% formalin/PBS solution until processing for standard histochemical analysis. Five sections are cut from each stent; 1 mm proximal to the stent, 1 mm from the proximal end of the stent, mid-stent, 1 mm from the distal edge of the stent and 1 mm distal to the stent. Sections are stained with hematoxylin & eosin (HE) and elastin trichrome. Inflammatory [Kornowski Score (0-3)] scores are determined to assess for evidence of rejection of the delivered cells. After the index procedure (about 28 days), the animals are anesthetized and coronary angiography is performed through an arteriotomy in the right carotid artery. Quantitative coronary angiography is performed and the vessels interrogated using IVUS, and changes in vessel caliber recorded using standard clinical algorithms.

Example 11

Transfection of Mammalian Cells In Vitro for Use in Blood Vessel Remodeling

Progenitor endothelial cells are transfected using electroporation of a bicistronic plasmid containing genes encoding a protein responsible for the production of adenosine and a prostate specific cell membrane protein. Both genes are under the control of their own promoter, so that the genes are expressed constitutively.

A vector is constructed similarly as described above comprising a gene encoding a prostatic specific membrane protein comprising its native promoter and a gene encoding α-CGRP with an SV40 promoter for overexpression is arranged in tandem within the same expression vector. The plasmid construct can be used to transfect cells mammalian cells for use in patients as describe in Example 9. Cells are infused into the patient's circulation subsequently after implantation of a coated medical device near the site of implantation.

Figures 23A, 23B:
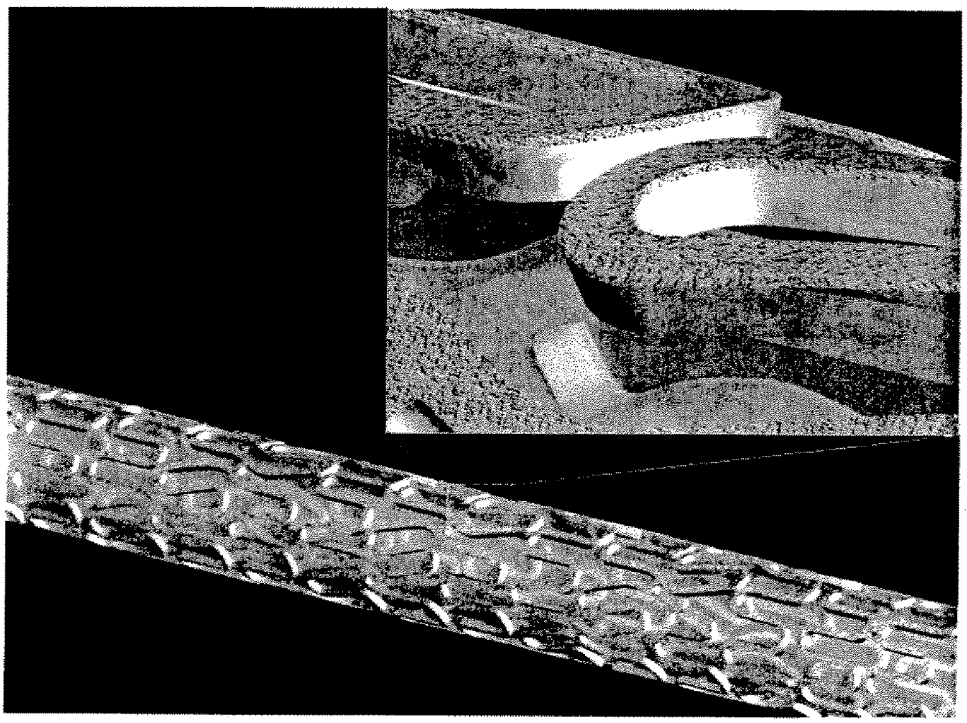
FIGS. 23A and 23B are scanning electron micrographs of a stent having a porous coating formed of a non-polymer matrix comprising nanoparticles made of a metallic alloy.

In an embodiment illustrated with respect to FIGS. 23A and 23B, there is depicted a medical device having a coating comprising a matrix formed of a non-porous material. In particular, FIGS. 23A and 23B show scanning electron micrographs of an exemplar stainless steel stent having a porous coating formed of a matrix formed of nanoparticles made from a metallic alloy. As seen in the figures, the outer surface of the stent's struts which will contact adjacent tissue when the stent is implanted into a vessel is coated with the matrix.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An implantable medical device having a luminal surface and a coating; wherein the coating comprises (a) one or more layers of a matrix; (b) one or more pharmaceutical substances that inhibit smooth muscle cell proliferation and/or migration, and (c) a ligand attached to the matrix, wherein the ligand is an antibody, an antibody fragment or a combination thereof, and wherein the antibody or antibody fragment specifically binds to a cell surface marker of endothelial progenitor cells and/or endothelial cells and captures circulating endothelial progenitor cells and/or endothelial cells on the luminal surface of the device after implantation of the device.

2. The implantable medical device of claim 1, wherein the medical device is a stent, a vascular graft, a synthetic graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port.

3. The implantable medical device of claim 1, wherein the matrix comprises a porous material comprising nanoparticles.

4. The implantable medical device of claim 3, wherein the nanoparticles comprise a metal, or a metallic alloy.

5. The implantable medical device of claim 1, wherein the cell surface marker is selected from the group consisting of CD133, CD45, CD34, CD31, CD14, CDw90, CD117, VEGFR-1, VEGFR-2, Muc-18 (CD146), CD130, stem cell antigen (Sca-1), stem cell factor 1 (SCF/c-Kit ligand), Tie-2, MHC H-2Kk, HLA-DR, and a combination thereof.

6. The implantable medical device of claim 1, wherein the matrix is formed of nanoparticles having porous openings of from about 5 nm to about 5 μm in diameter and the ligand is an antibody, antibody fragments or combinations thereof.

7. The implantable medical device of claim 1, wherein the antibody or antibody fragment is anti-CD34 or anti-CD133.

8. The implantable medical device of claim 1, wherein said one or more pharmaceutical substance(s) is/are selected from the group consisting of peroxisome proliferator-activated receptor-alpha agonists, peroxisome proliferator-activated receptor-delta agonists, peroxisome proliferator-activated receptor-gamma agonists, calcitonin gene related peptide (o-CGRP), monocyte chemoattractant protein-1, adenosine, prostacyclins, tachykinins, sialokinins, neurokinins, aromatase inhibitors, plasminogen activator, erythropoietin, darbepotin, serine proteinase-1 (SERP-1), metalloproteinases, and a combination thereof.

9. The implantable medical device of claim 1, wherein said one or more pharmaceutical substance(s) is/are selected from the group consisting of rapamycin, a rapamycin derivative, everolimus, sirolimus, biolimus, biolimus A-9, paclitaxel, and a combination thereof.

10. A method for treating vascular disease, comprising the step of implanting into a patient in need of treatment an implantable medical device, wherein the medical device has a luminal surface and a coating, wherein the coating comprises (a) one or more layers of a matrix; (b) one or more pharmaceutical substances that inhibit smooth muscle cell proliferation and/or migration, and (c) a ligand attached to the matrix, wherein the ligand is an antibody, an antibody fragment or a combination thereof, wherein the antibody or antibody fragment specifically binds to a cell surface marker of endothelial progenitor cells and/or endothelial cells, and wherein the ligand captures circulating endothelial progenitor cells and/or endothelial cells on the luminal surface of said medical device after implantation into said patient.

11. The method of claim 10, wherein the matrix is formed of a porous material comprising nanoparticles.

12. The method of claim 11, wherein the nanoparticles comprise a metal, or a metallic alloy.

13. The method of claim 10, wherein the cell surface marker is selected from the group consisting of CD133, CD45, CD34, CD31, CD14, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, and MHC H-2Kk.

14. The method of claim 10, wherein the matrix comprises nanoparticles having porous openings of from about 5 nm to about 5 μm in diameter.

15. The method of claim 10, wherein the antibody or antibody fragment is anti-CD34 or anti-CD133.

* * * * *